(12) United States Patent
Huang et al.

(10) Patent No.: US 11,491,184 B2
(45) Date of Patent: Nov. 8, 2022

(54) LIQUIDS RICH IN NOBLE GAS AND METHODS OF THEIR PREPARATION AND USE

(71) Applicant: THE BOARD OF REGENTS OF THE UNIVERSITY OF TEXAS SYSTEM, Austin, TX (US)

(72) Inventors: Shao-Ling Huang, Houston, TX (US); David McPherson, Houston, TX (US); Yong-Jian Geng, Houston, TX (US); Xing Yin, Houston, TX (US); Hyunggun Kim, Houston, TX (US); Melvin Klegerman, Houston, TX (US); Tao Peng, Houston, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 16/702,164

(22) Filed: Dec. 3, 2019

(65) Prior Publication Data
US 2020/0215100 A1 Jul. 9, 2020

Related U.S. Application Data

(63) Continuation of application No. 15/695,735, filed on Sep. 5, 2017, now abandoned, which is a continuation of application No. 14/775,907, filed as application No. PCT/US2014/030210 on Mar. 17, 2014, now abandoned.

(60) Provisional application No. 61/889,901, filed on Oct. 11, 2013, provisional application No. 61/788,808, filed on Mar. 15, 2013.

(51) Int. Cl.
| | |
|---|---|
| A61K 33/00 | (2006.01) |
| A61K 47/02 | (2006.01) |
| A61K 9/00 | (2006.01) |
| A23L 33/16 | (2016.01) |
| A61K 47/69 | (2017.01) |
| A61K 47/42 | (2017.01) |
| A61K 47/24 | (2006.01) |
| A61K 47/14 | (2017.01) |
| A61K 9/107 | (2006.01) |
| A61K 47/44 | (2017.01) |
| A23D 7/005 | (2006.01) |
| A23L 33/115 | (2016.01) |
| A23L 33/25 | (2016.01) |
| A61J 1/14 | (2006.01) |
| A61K 47/28 | (2006.01) |

(52) U.S. Cl.
CPC ............ *A61K 33/00* (2013.01); *A23D 7/0053* (2013.01); *A23L 33/115* (2016.08); *A23L 33/16* (2016.08); *A23L 33/25* (2016.08); *A61J 1/1468* (2015.05); *A61K 9/0095* (2013.01); *A61K 9/107* (2013.01); *A61K 47/02* (2013.01); *A61K 47/14* (2013.01); *A61K 47/24* (2013.01); *A61K 47/28* (2013.01); *A61K 47/42* (2013.01); *A61K 47/44* (2013.01); *A61K 47/6951* (2017.08); *A23V 2002/00* (2013.01)

(58) Field of Classification Search
CPC ....... A61K 47/02; A61K 2300/00; A61P 9/12; A61P 9/10; A61P 9/00; A61P 9/04; A23V 2020/00; A23V 2250/00; A23V 2250/10; A23V 2250/18
See application file for complete search history.

(56) References Cited

U.S. PATENT DOCUMENTS

| | | | |
|---|---|---|---|
| 5,228,446 | A | 7/1993 | Unger et al. |
| 5,498,421 | A | 3/1996 | Grinstaff et al. |
| 5,612,057 | A | 3/1997 | Lanza et al. |
| 5,639,441 | A | 6/1997 | Sievers et al. |
| 5,670,177 | A | 9/1997 | Briend et al. |
| 5,769,080 | A | 6/1998 | Unger et al. |
| 5,853,752 | A | 12/1998 | Unger et al. |
| 5,858,399 | A | 1/1999 | Lanza et al. |
| 6,050,444 | A | 4/2000 | Sugg |
| 6,123,919 | A | 9/2000 | Albert et al. |
| 6,241,966 | B1 | 6/2001 | Albert et al. |
| 6,274,633 | B1 | 8/2001 | Franks et al. |
| 6,443,898 | B1 | 9/2002 | Unger et al. |
| 6,559,190 | B1 | 5/2003 | Petzelt et al. |
| 6,576,220 | B2 | 6/2003 | Unger |
| 6,653,354 | B2 | 11/2003 | Franks et al. |
| 7,235,264 | B2 | 6/2007 | Neu et al. |
| 7,390,508 | B2 | 6/2008 | Franks et al. |
| 7,405,241 | B2 | 7/2008 | Lemaire |
| 7,442,383 | B2 | 10/2008 | Franks et al. |
| 7,632,872 | B2 | 12/2009 | Franks et al. |

(Continued)

FOREIGN PATENT DOCUMENTS

| | | |
|---|---|---|
| CN | 1255065 | 5/2000 |
| CN | 1668315 | 9/2005 |

(Continued)

OTHER PUBLICATIONS

Esencan et al, title:Xenon is medical area, Medical gas research, vol. 3, No. 4, 2013) (Year: 2013).*

(Continued)

Primary Examiner — Katherine Peebles
(74) Attorney, Agent, or Firm — Parker Highlander PLLC

(57) ABSTRACT

Provided herein is a novel composition for oral administration and delivery of Noble gas, such as xenon or argon. Methods of treating and preventing neuronal or cardiovascular damage with such compositions are also provided.

12 Claims, 16 Drawing Sheets

(56) References Cited

U.S. PATENT DOCUMENTS

| | | | |
|---|---|---|---|
| 7,700,135 B2 | 4/2010 | Neu et al. | |
| 7,976,743 B2 | 7/2011 | Huang et al. | |
| 8,143,317 B2 | 3/2012 | Petzelt et al. | |
| 2001/0031243 A1 | 10/2001 | Unger | |
| 2002/0044994 A1 | 4/2002 | Spencer | |
| 2002/0052573 A1 | 5/2002 | Georgieff | |
| 2003/0180375 A1 | 9/2003 | Petzelt et al. | |
| 2004/0127462 A1 | 7/2004 | Bougaret et al. | |
| 2004/0166064 A1 | 8/2004 | Gilkerson et al. | |
| 2005/0238726 A1 | 10/2005 | Franks et al. | |
| 2005/0244508 A1 | 11/2005 | Neu et al. | |
| 2005/0255169 A1 | 11/2005 | Pilger et al. | |
| 2008/0069924 A1* | 3/2008 | Zeller | A21D 2/18 426/512 |
| 2008/0175893 A1 | 7/2008 | Huang et al. | |
| 2008/0187605 A1 | 8/2008 | Olney | |
| 2008/0305156 A1 | 12/2008 | Laing et al. | |
| 2009/0041833 A1 | 2/2009 | Bettinger et al. | |
| 2009/0311340 A1 | 12/2009 | Franks et al. | |
| 2010/0196461 A1 | 8/2010 | Simpkins | |
| 2010/0278942 A1 | 11/2010 | Abraini | |
| 2010/0291056 A1 | 11/2010 | Mosher et al. | |
| 2010/0316729 A1 | 12/2010 | Franks et al. | |
| 2011/0027378 A1 | 2/2011 | Pendharkar et al. | |
| 2011/0104052 A1 | 5/2011 | Barnett et al. | |
| 2011/0176994 A1 | 7/2011 | Pratt et al. | |
| 2011/0177159 A1 | 7/2011 | Wu | |
| 2011/0250183 A1 | 10/2011 | Picard et al. | |
| 2012/0045528 A1 | 2/2012 | Bessiere et al. | |
| 2013/0039993 A1 | 2/2013 | Lemaire | |
| 2015/0216800 A1 | 8/2015 | Huang et al. | |

FOREIGN PATENT DOCUMENTS

| | | |
|---|---|---|
| DE | 199 33 704 | 1/2001 |
| DE | 103 28 272 | 1/2004 |
| DE | 103 36 768 | 2/2004 |
| DE | 103 36 778 | 2/2004 |
| EP | 0070368 | 1/1983 |
| EP | 0587869 B1 * | 5/1997 |
| EP | 1 160 018 | 1/2002 |
| EP | 0 677 332 | 2/2002 |
| EP | 1 187 635 | 2/2004 |
| EP | 0 616 508 | 9/2004 |
| EP | 1 228 770 | 7/2005 |
| EP | 1 994 935 | 11/2008 |
| EP | 1 499 329 | 5/2012 |
| IT | MI20071031 | 11/2008 |
| JP | S58-18342 | 2/1983 |
| JP | H8-507075 | 7/1996 |
| JP | 2004-531525 | 10/2004 |
| WO | WO 94/18954 | 9/1994 |
| WO | WO 97/37239 | 10/1997 |
| WO | WO 2001/008692 | 2/2001 |
| WO | WO 02/22141 | 3/2002 |
| WO | WO 2002/045721 | 6/2002 |
| WO | WO-2002045721 * | 6/2002 |
| WO | WO 03/105871 | 12/2003 |
| WO | WO 2005/067945 | 7/2005 |
| WO | WO 2012/020030 | 2/2012 |
| WO | WO 2012/096697 | 7/2012 |

OTHER PUBLICATIONS

Mills, title: Pharmaceutical excipients, overview; presented Jun. 21, 2010). (Year: 2010).*
Goto, et al; title: Cardiovascular effects of xenon and nitrous oxide inpatients during fentanyl-midazolam anaesthesia; Anesthesia, 2004, 59, pp. 1178-1183. (Year: 2004).*
Jared A. Silverman, et al; title: L Inhibition of Daptomycin by Pulmonary Surfactant: In Vitro Modeling and Clinical Impact; The Journal of Infectious Diseases, vol. 191, Issue 12, Jun. 15, 2005, pp. 2149-2152. (Year: 2005).*
Huntjens, et al; title: Correlation between in vitro and in vivo concentration-effect relationships of naproxen in rats and healthy volunteers; British Journal of Pharmacology; vol. 148, pp. 396-404; published online May 8, 2006. (Year: 2006).*
Vyas et al; title: cyclodextrin based novel drug delivery systems; J. Incl Phenom Macrocycl chem.; vol. 62, pp. 23-42, published online: May 23, 2008 (Year: 2008).*
Houser et al, title: Animal model of heart failure, attached non-patent literature; Circulation Research. 2012; vol. 111, pp. 131-150; published May 17, 2012. (Year: 2012).*
Shin et al, title:Current Status and Limitations of Myocardial Infarction Large Animal Models in Cardiovascular Translational Research d Animal model of heart failure, Front. Bioeng. Biotechnol., Apr. 29, 2021 (Year: 2021).*
Badimon et al; title: Atherosclerosis, platelets and thrombosis in acute ischemic heart disease; European Heart Journal: Acute Cardiovascular Care; vol. 1(1); pp. 60-74. 2012 (Year: 2012).*
Computer Translation of WO 02/22141, generated on Dec. 13, 2018.
Gao, Lan, et al. "Postoperative cognitive dysfunction after cardiac surgery." Chest 128.5 (2005): 3664-3670.
Lloyd et al., "Xenon reduces apoptosis, γ- and β-secretase expression in an in vitro model of Alzheimer's disease", Br. J. Anaesth. (2011) vol. 106, No. 3, p. 436P.
Office Communication issued in Japanese application No. 2016-503348, dated Dec. 10, 2018. Original and English Translation.
Office Communication issued in Japanese application No. 2016-503348, dated Sep. 30, 2019. Original and English Translation.
Ballantyne, Christie M., and Vijay Nambi. "Markers of inflammation and their clinical significance." Atherosclerosis Supplements 6.2 (2005): 21-29.
Baumert et al. "The effect of xenon anesthesia on the size of experimental myocardial infarction." Anesthesia & Analgesia 105.5 (2007): 1200-1206.
Britton et al., "In vivo therapeutic gas delivery for neuroprotection with echogenic liposomes", Circulation, 122(16): 1578-1587, 2010.
David et al., "Xenon is an inhibitor of tissue-plasminogen activator: adverse and beneficial effects in a rat model of thromboembolic stroke", Journal of Cerebral Blood Flow and Metabolism, 30(4): 718-728, 2010.
Eckert et al., "Liposome-incorporated DHA increases neuronal survival by enhancing non-amyloidogenic APP processing", Biochimica et Biophysica Acta, 1808: 236-243, 2011.
Esencan, Ecem et al. "Xenon in medical area: emphasis on neuroprotection in hvpoxia and anesthesia."Medical gas research 3.1 (2013): 4.
Extended European Search Report issued in European Application No. 14765333.1, dated Oct. 6, 2016.
Geraldes, Pedro, and George L. King. "Activation oi protein kinase C isoloims and its impact on diabetic complications." Circulation Research 106.8 (2010): 1319-1331.
Gerth et al., "Applicability of Henry's law to hydrogen, helium, and nitrogen solubilities in water and olive oil at 37 ° C. and pressures up to 300 atmospheres", Archives of Biochemistry and Biophysics, 241(1): 187-199, 1985.
International Preliminary Report on Patentability issued in International Application No. PCT/US2013/054349, dated Feb. 10, 2015.
International Preliminary Report on Patentability issued in International Application No. PCT/US2014/030210, dated Sep. 15, 2015.
International Search Report and Written Opinion issued in International Application No. PCT/US2013/054349, dated Aug. 20, 2014.
International Search Report and Written Opinion issued in International Application No. PCT/US2014/030210, dated Oct. 17, 2014.
Liu, Wenwu, et al. "Xenon preconditioning: molecular mechanisms and biological effects."Medical gas research 3.1 (2013): 3.
Mills, Simon, "Pharmacuetical excipients—an overview including considerations for paediatric dosing." World Health Organization; Training Workshop. Beijing, Jun. 21-25, 2010.
Office Communication issued in Australian application No. 2014233018, dated Mar. 29, 2018.
Office Communication issued in Chinese application No. 201210356929. 9, dated Nov. 15, 2014.

(56) References Cited

OTHER PUBLICATIONS

Office Communication issued in Chinese Application No. 201480014964.X, dated Jun. 12, 2017. (English Translation and Original).
Office Communication issued in Chinese application No. 201480014964.X, dated Apr. 4, 2018. (English Translation).
Office Communication issued in Chinese application No. 201480014964.X, dated Nov. 27, 2018. English Translation.
Office Communication issued in Chinese patent application No. 201210356929.9, dated Oct. 12, 2015.
Office Communication issued in European Application No. 14765333.1, dated Sep. 9, 2019.
Office Communication issued in Japanese application No. 2016-503348, dated Jan. 31, 2018. (English Translation and Original).
Office Communication issued in Japanese application No. 2016-503348, dated Dec. 10, 2018. English Translation.
Office Communication issued in U.S. Appl. No. 15/695,735, dated Jul. 3, 2019.
Peng et al., "Abstract 3977: Neuroprotective effects of echogenic liposomes-mediated xenon delivery in a rat embolic stroke model combined with tissue plasminogen activator thrombolysis", International Stroke Conference Poster Abstracts, 43:A3977, 2012.
Preckel, Benedikt, et al. "Molecular mechanisms transducing the anesthetic, analgesic, and organ-protective actions of xenon." *Anesthesiology: The Journal of the American Society of Anesthesiologists* 105.1 (2006): 187-197.
Servick. K. "Another major drug candidate targeting the brain plaques of Alzheimer's disease has failed. What's left." *Science* 10 (2019).
Shaw et al., "Ultrasound-enhanced thrombolysis with tPA-loaded echogenic liposomes", *Thrombosis research*, 124(3): 306-310, 2009.
Wood, David, and Roger Caputi. *Solubilities of Kr and Xe in fresh and sea water*. No. USNRDL-TR-988. Naval Radiological Defense Lab San Francisco CA, 1966.
Ansari, Khalid A., et al. "Cyclodextrin-based nanosponges for delivery of resveratrol: in vitro characterisation, stability, cytotoxicity and permeation study." *Aaps Pharmscitech* 12.1 (2011): 279-286.
Office Communication issued in Japanese application No. 2016-503348, dated Jan. 6, 2021. Original and English Translation.
Meir, Karen S., et al. "Atherosclerosis in the Apolipoprotein E-Deficient Mouse" Arterioscler Thromb Vasc Biol. (2004) 24:1006-1014.

\* cited by examiner

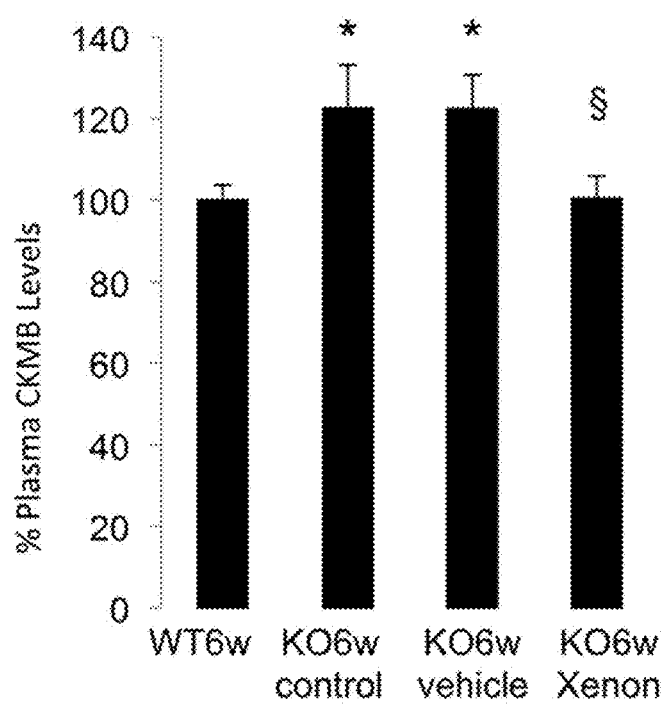
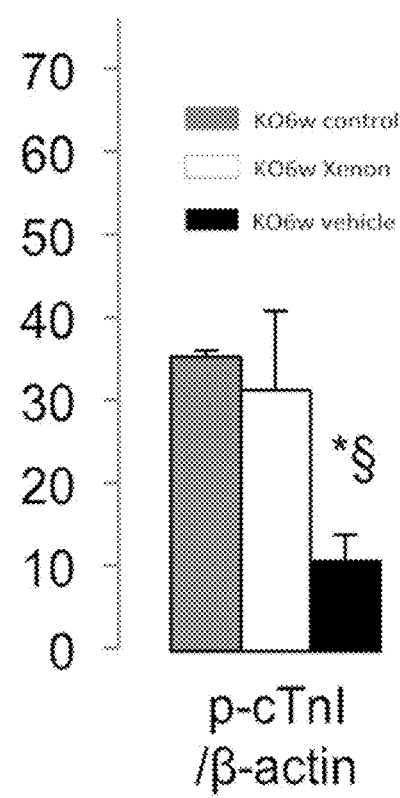
FIG. 13A
FIG. 13B

LIQUIDS RICH IN NOBLE GAS AND METHODS OF THEIR PREPARATION AND USE

This application is a continuation of U.S. patent application Ser. No. 15/695,735, filed Sep. 5, 2017, which is a continuation of U.S. patent application Ser. No. 14/775,907, filed Sep. 14, 2015, as a national phase application under 35 U.S.C. § 371 of International Application No. PCT/US2014/030210, filed Mar. 17, 2014, which claims the benefit of U.S. Provisional Patent Application Nos. 61/788,808, filed Mar. 15, 2013, and 61/889,901, filed Oct. 11, 2013, all of which are incorporated herein by reference in their entirety.

The invention was made with government support under Grant Nos. NS067454, HL074002, and HL059586 awarded by the National Institutes of Health. The government has certain rights in the invention.

BACKGROUND OF THE INVENTION

1. Field of the Invention

The present invention relates generally to the fields of molecular biology, medicine and nutraceuticals. More particularly, it concerns methods for oral delivery of inert gas compositions, such as Xenon or Argon, for the treatment and prevention of disease.

2. Description of Related Art

Both Xenon (Xe) and Argon (Ar) are, pleiotypic cytoprotective gases, which have unique advantages that include rapid diffusion across biological barriers such as the blood-brain barrier (BBB) and complete passage across cell membranes due to its low blood-gas partition coefficient. In animal models, Xe given as a continuous gas inhalation has demonstrated potent neuroprotective and myocardical protective effects. Xe protects against oxygen and glucose deprivation (OGD) and protects against hypoxia/ischemia by alteration of molecules involved in neuronal ischemic tolerance. Xe helps to induce transcription of several pro-survival genes including brain-derived neurotrophic factor (BDNF) and pro-survival proteins such as $Bcl_2$ which promote cell tolerance to ischemic injury. Xe interacts with the human immune system by modulating inflammatory cytokines such as TNF-α and IL-6 in monocytes. Xe helps to sustain release of hypoxia inducible factor 1 alpha (HIF-1α) and other proteins. All these pathways are implicated in organ protection.

Current methods for gas delivery involve inhalation and administration of a gas donor. However, Xe or Ar inhalation cannot be practically given in many situations as the required high Xe or Ar concentration for inhalation limits the fraction of inspired oxygen necessary for cell survival. In addition, there is the difficulty of developing a continuous inhalation strategy for patients as daily use. Improved methods of delivery of Xe or Ar are greatly needed.

SUMMARY OF THE INVENTION

Embodiments of the present invention relates generally to treatment methods, pharmaceuticals and nutraceuticals (a portmanteau of the words "nutrition" and "pharmaceutical", which is a food or food product with health and medical benefits, including the prevention and treatment of disease). More particularly, it concerns methods for primarily oral delivery of inert gas compositions to the gastrointestinal tract (GI), comprising a Noble gas such as Helium, Neon, Argon, Krypton and/or Xenon. Such gases can be delivered as part of a method for the prevention and/or treatment of diseases in the heart and brain, including but not limited to atherosclerosis-associated ischemic heart disease, stroke and other neuron degenerative condition, such as dementia (e.g., Alzheimer disease). In certain aspects, compositions comprising Noble gases provide reduction in one or more marker of inflammation or general improvement in well-being.

In a first embodiment there is provided a liquid (or semi-liquid, e.g., pastes or gels) formulation having an enhanced concentration of encapsulated Noble gas (e.g., the gas may be encapsulated to achieve a specified concentration). The Noble gas can be selected from Helium, Neon, Argon, Krypton, Xenon or a mixture thereof. As used herein the encapsulated Noble gas can be provided as a gas dissolved in a lipid and emulsified, encapsulated in a liposome formulation and/or encapsulated in a water soluble molecule (e.g., cyclodextrin). In general the encapsulation allows the composition to achieve a higher gas content than can be achieved in an equal amount of water (absent such encapsulation) and the same temperature and pressure. In preferred aspects, the composition is formulated for oral delivery.

In a certain embodiments there is provided a nutraceutical (such as a beverage) composition comprising a substantially aqueous component and a dissolved Noble gas, wherein a portion of the Noble gas in encapsulated to enhance aqueous solubility. In some aspects, the encapsulated Noble gas may be encapsulated in a lipid, such as in a liposome or in a lipid phase that is emulsified in the composition. In still further aspects, the Noble gas (e.g., Xe Ar, Kr, Ne or He) is encapsulated in a water-soluble molecule, such as a water soluble polymer. In still further aspects, the Noble gas is encapsulated in α-, β-, or γ-cyclodextrin or a mixture thereof. Further molecules that may be used for Noble gas encapsulation are detailed below.

In yet a further embodiment the invention provides single serving nutraceutical composition including but not limited to beverages, gels, pastes, tablets, and capsules. For example, the composition may comprise about 1, 2, 3, 4, 5 or 10 to about 15, 20, 25, 30, 35, 40, 45 or 50 ml of the composition. In further aspects, the composition may comprise about 10, 15, 25, 30, 35, 40, 45 or 50 to about 100, 150, 200, 250, 300, 350, 400, 450 or 500 ml of a composition (e.g., a substantially aqueous composition). In some aspects, a composition of the embodiments comprises 0.01 to 15 g or about 0.1 to 200 mg of dissolved Noble gas (or a mixture of two or more such gases), wherein a portion of the Noble gas is encapsulated to enhance aqueous solubility. As detailed above the Noble gas may be encapsulated or solubilized in a (emulsified) lipid component, in a liposome or in a water-soluble molecule. For example, in some aspects, the Noble gas (e.g., Xe) is encapsulated in a water-soluble polymer, such as cyclodextrin. In certain aspects, the amount of dissolved Noble gas (e.g., Xe) in the formulation is about 0.1 mg to 10 g, 0.1 to 1,000 mg, 0.1 to 500 mg, 0.5 to 100 mg, 1 to 100 mg, 1 to 50 mg, 1 to 25 mg or 1 to 10 mg. Likewise, the volume of liquid component in the formulation can be adjusted to provide an optimal amount of the Noble gas in a single serving. For example, the single serving beverage may comprise a total volume of between about 1 to 10 ml, 10 to 25 ml, 25 to 50 ml, 50 to 500 ml, 50 to 300 ml, 100 to 300 ml or 200 to 400 ml. As detailed further herein, in certain preferred embodiments, such a single serving nutraceutical is provided in a gas-impermeable sealed container, such as a bottle, can or foil or polymer package. Likewise, in some aspects, a package of single-serving nutraceutical beverages is provided comprising 4, 6, 8, 12, 24 or more single serving compositions such as beverages, each comprised in a separate sealed container.

As detailed supra, certain aspects of the embodiments concern compositions comprising Noble gases (e.g., Xe), at least a portion of which is encapsulated in cyclodextrin (CD) (e.g., β-cyclodextrin). In some cases, cyclodextrin for use according to the embodiments will include hydrophilic groups that further enhance the aqueous solubility. For example, in certain aspects, the CD is a hydroxypropyl-CD, such as hydroxypropyl-beta-cyclodextrin. A composition may comprise, for instance, about 0.01 to about 5.0 mg/ml; about 0.05 to about 2.0 mg/ml; about 0.1 to about 1.5 mg/ml or about 0.1 to about 1.0 mg/ml of a CD. In some specific aspects, the composition comprises 0.1 to about 1.0 mg/ml of hydroxypropyl β-CD. In still further aspects, a composition comprises about 0.1 to about 5.0 ml; about 0.1 to about 4.0; about 0.1 to about 3.8; about 0.1 to about 2.0; about 0.1 to about 1.0 ml; or 0.5 to about 1.0 ml of Noble gas (e.g., Xe) per 0.5 mg of cyclodextrin in the composition (e.g., at standard temperature-pressure). In particular, a composition may comprise about 0.1 to about 5.0 ml; about 0.1 to about 4.0; about 0.1 to about 3.8; about 0.1 to about 2.0; about 0.1 to about 1.0 ml; or 0.5 to about 1.0 ml of Xe per 0.5 mg of β-cyclodextrin (e.g., hydroxypropyl β-CD). In a very specific aspect, a composition comprises up to about 3.8 ml of Xe to 0.5 mg of a CD molecule (e.g., per ml of water).

Additional cyclodextrin molecules that can be used according to the embodiments (in either oil or water compositions depending on the desired solubility) include, without limitation, methyl-β-cyclodextrin, randomly methylated-β-cyclodextrin, dimethyl-β-cyclodextrin, randomly dimethylated-β-cyclodextrin, trimethyl-β-cyclodextrin, acetylated dimethyl-β-cyclodextrin, 2-Hydroxyethyl-β-cyclodextrin, 2-Hydroxypropyl-β-cyclodextrin, 3-Hydroxypropyl-β-cyclodextrin, hydroxybutenyl-β-cyclodextrin, 2,3-Dihydroxypropyl-β-cyclodextrin, 2-Hydroxypropyl-γ-cyclodextrin, glucosyl-β-cyclodextrin, maltosyl-β-cyclodextrin, glucuronyl-glucosyl-β-cyclodextrin, alkylated O-cyclodextrin, 2,6-Di-O-ethyl-β-cyclodextrin, 2,3,6-Tri-O-ethyl-β-cyclodextrin, acylated β-Cyclodextrin, 2,3,6-Tri-O-acyl(C2-C18)-β-cyclodextrin, 2,3,6-Tri-O-butanoyl-O-cyclodextrin, 2,3,6-Tri-O-valeryl-O-cyclodextrin, 2,3,6-Tri-O-octyl-β-cyclodextrin, O-Carboxymethyl-O-ethyl-β-cyclodextrin, β-Cyclodextrin sulfate, sulfobutyl ether group-β-cyclodextrin, or sulfobutyl ether group-β-cyclodextrin.

The methodologies demonstrated herein can provide very high concentrations of Noble gas in a liquid format. However, in some cases, liquids or semi-liquids (including e.g., a beverage) of the embodiments may comprise a relatively moderate amount of a Noble gas such as Xe. For example, such a beverage may comprise a dissolved Xe concentration (when in a sealed container) of about 1.0 to about 5,000 µg/ml, about 10 to about 1,000 µg/ml, about 100 to about 800 µg/ml, about 1.0 to about 100 µg/ml, 5.0 to about 50 µg/ml, about 10 to about 100 µg/ml or about 10 to about 50 µg/ml. For example, Xe dissolved in water at standard temperature and pressure can have a concentration of about 600 µg/ml. In a further aspect, a beverage is provided having a high concentration of Xe, such as about 1 mg/ml to about 100 mg/ml, 1 mg/ml to about 50 mg/ml, about 1 mg/ml to about 30 mg/ml, or about 10 mg/ml to about 50 mg/ml. In some aspects, a beverage is provided comprising a Xe level of about 10 mg/ml to about 15, 20, 25, 30, 35, 40, 45 or 50 mg/ml Xe (e.g., such as a beverage comprising pressurized and/or encapsulated Xe). For example, a formulation comprising cyclodextrin (hydroxypropyl β-CD) encapsulated Xe can have a Xe concentration of about 22.4 mg/ml when formulated at 3 atm and 4° C., then brought to standard ambient temperature and pressure (SATP)).

In some aspects, the methodologies and compositions herein concern Argon gas provided in a liquid or semi-liquid format (e.g., as a beverage). For example, such a composition may comprise a dissolved Ar concentration (when in a sealed container) of about 1.0 to about 1,000 µg/ml, about 10 to about 500 µg/ml, about 20 to about 500 µg/ml, about 30 to about 250 µg/ml, about 40 to about 200 µg/ml, about 50 to about 100 µg/ml or about 40 to about 75 µg/ml. For example, Ar dissolved in water at standard temperature and pressure can have a concentration of about 55 µg/ml. In a further aspect, a beverage is provided having a high concentration of Ar (such as Ar encapsulated in a polymer or an oil), such as about 0.01 µg/ml to about 1 mg/ml, 0.1 µg/ml to about 1 mg/ml, about 1 µg/ml to about 500 µg/ml, about 10/ml to about 500 µg/ml, about 100 µg/ml to about 500 µg/ml, or about 200 µg/ml to about 500 µg/ml. For example, a formulation comprising an oil encapsulated Ar at SATP may have an Ar concentration of about 165 µg/ml.

In still yet a further aspect, a composition of the embodiments is characterized in having a Noble gas content (at standard ambient temperature and pressure; SATP) of at least about 0.5 mM, 0.6 mM, 0.7 mM, 0.8 mM, 0.9 mM, 1.0 mM, 1.1 mM, 1.2 mM, 1.3 mM, 1.4 mM, 1.5 mM, 1.6 mM, 1.7 mM, 1.8 mM, 1.9 mM or 2.0 mM. In some aspects, the Noble gas is in a concentration of at least 4.5, 4.6., 4.7, 4.8, 4.9 or 5.0 mM. Thus, in some aspects, the composition comprises a Noble gas content of between about 5.0 and 50 mM, 5.0 and 25 mM, 5.0 and 20.0 mM, 5.0 and 15 mM or 5.0 and 10 mM at SATP. In still further aspects, the composition comprises a Xenon content of greater than about 5.0 mM, such as between about 5.0 and 50 mM, 5.0 and 25 mM, 5.0 and 20.0 mM, 5.0 and 15 mM or 5.0 and 10 mM at SATP. In still further aspects, a composition comprises Ar at a concentration of greater than 0.5 mM, 0.6 mM, 0.7 mM, 0.8 mM, 0.9 mM, 1.0 mM, 1.1 mM, 1.2 mM, 1.3 mM, 1.4 mM, 1.5 mM, 1.6 mM, 1.7 mM, 1.8 mM, 1.9 mM or 2.0 mM. For example, the composition may comprise between about 1.0 and 10 mM, 1.5 and 10 mM, 1.5 and 10 mM, 2.0 and 10 mM or 2.0 and 5 mM Ar at SATP.

In still further aspects, a composition of the embodiments is defined by the Noble gas content as compared to the aqueous component (e.g., water) content. For example, a composition may comprise a Noble gas to aqueous component ratio of between about 1:20 and 4:1; about 1:10 and 4:1; about 1:9 and 4:1; about 1:2 and 4:1; 1:1 and 4:1; about 1.5:1 and 4:1; about 1:20 and 1:1; about 1:10 and 1:1; or about 2:1 and 3:1 (volume:volume). In some aspects, the Noble gas to aqueous component ratio is greater than 1:10; 1:9; or 1:5. In certain aspects, the Noble gas to aqueous component ratio is greater than 1:1 or greater than 2:1. Thus, in some specific aspects, a composition comprises a Xe to water ratio of between about 1:2 and 4:1; 1:1 and 4:1 or 1.5:1 and 4:1 or 2:1 and 3:1 (volume:volume), such as a ratio greater than about 2:1.

In certain embodiments compositions such as a beverage composition of the embodiments further comprise additional components such as preservatives, flavoring agents, dyes, vitamins, anti-oxidants, plant or microbial extracts, salts (electrolytes, glycerol, sodium, potassium and chloride), alcohols, lipids, oils, or a mixture thereof. Thus, in some aspects, a beverage or other form of the embodiments is further defined as an herbal, vitamin or energy-providing nutraceutical composition.

In a further embodiment the invention provides, a pharmaceutical or nutraceutical composition comprising lipids such as an edible oil component comprising a soluble gas, such as Noble gas (e.g., xenon or argon gas). Examples, of oils for such a composition include, without limitation, flaxseed oil, rapeseed oil, soybean oil, walnut oil, fish oil, safflower oil, sunflower oil, corn oil, cotton seed oil, peanut oil, palm oil or olive oil. In one aspect, the oil may comprise polyunsaturated fatty acids (PUFA), such as an oil comprising at least 5%, 10%, 20%, 30%, 40%, 50%, 60%, 70%, 80%, 90% or more PUFAs. In still further aspects, the oil comprises omega-3 fatty acids, which may aid in biological uptake of the gases of the embodiments. In still further aspects, the oil component is saturated or super saturated with xenon or argon gas.

In a further embodiment, an oil-gas composition may be further comprised in an emulsion. For example, an emulsion can comprise (a) 25% to 50%, 60%, 70%, 80%, 90%, 95% or more by volume oil, (the oil comprising soluble xenon or argon gas) and (b) 1%, 2%, 3%, 5%, 10%, 20%, or 30% to about 75% or 85% by volume aqueous solution. In some aspects, the aqueous solution comprises water (e.g., spring water), fruit juice, vegetable juice or other nutritious beverage. In some aspects, the composition may further comprise phospholipid, detergent, or protein components. In some aspects, the composition further comprises phospholipids, detergents, flavorings, dyes, emulsifiers, co-emulsifiers and/or protein components. For example, the detergent can be a plant surfactant, a synthetic detergent or a bile acid. In certain aspects, the detergent is lithocholic acid, deoxycholic acid, taurocholic acid, glycocholic acid, chenodeoxycholic acid, or cholic acid. Examples of phospholipids for use according to the embodiments include, without limitation, egg phosphocholine (egg PC), soybean PC, DPPC or DOPC. Proteins that may be included are, for example, milk protein, whey isolate protein, soy protein isolate, potassium caseinate, egg albumin, (Brown) rice protein, hydrolyzed beef protein isolate, pea protein isolate, hemp protein, or bovine serum albumin.

As detailed above, in certain aspects, oil compositions are provided that comprise both soluble and insoluble, trapped, or free gases and that may be in a liquid or semi-liquid form. Gases that may be included in such compositions include without limitation Noble gases (e.g., He, Ar, Kr, Ne or Xe), $CO_2$, nitrous oxide, isoflurane and servoflurane. In preferred embodiments, a lipid oil composition comprises soluble xenon or argon gas (and, in some cases, also comprise insoluble or free Xe or Ar or other Noble gas). In some aspects, a composition comprises low oxygen or nitrogen content, or is essentially free of these gases. In some aspects, the oil composition is semi-saturated or saturated with a gas. In still further aspects, a lipid oil can be supersaturated with a gas (e.g., such that the gas is bubbling out of the oil when exposed to the atmosphere). In some aspects, a lipid oil composition of the embodiments may comprise between about 10 and 500 mg of xenon per ml of oil (e.g., between about 10, 20, 30, 40, 50, 60, 70, 80, 90 or 100 mg and about 150, 200, 250, 300, 350, 400, 450 or 500 mg per ml of oil). For example, at SATP an oil may comprise about 0.1 to about 50; about 0.1 to about 20 or about 1 to about 15 mg of Xe per ml of oil.

In certain specific aspects, a composition of the embodiments may comprise (a) 25% to 50% by volume oil (e.g., olive oil or other desired lipid), (the oil comprising soluble xenon or argon gas); (b) 50% to 75% by volume water solution; (c) 10-30 mg/ml of a phospholipid (e.g., egg phosphocholine); (d) 10-50 mg/ml of a protein (e.g., BSA); and (e) 1-5 mg/ml of a detergent (e.g., lithocholic acid). In some aspects, the composition may further comprise a preservative, flavoring agent, vitamin, anti-oxidant, or plant extract.

In some aspects, compositions comprising Noble gases may be comprised in a gas impermeable container of any size or shape. In some cases, the container may be pressurized (e.g., pressurized with a Noble gas, such as xenon or argon gas). In some aspects, such a container may comprise a single serving or unit dosage of a composition (e.g., in a paste, a gel, a pill, a tablet or capsule). In other cases, a container can comprise multiple doses (e.g., a multiple dose bottle or a compartmentalized container). In this later case to may be preferable that the container be pressurized and comprise a one-way value to release the composition without exposing the entire content to the atmosphere. In still further aspects, such a container may comprise excess gas (e.g., argon or xenon) that maintain the pressure in the vessel when doses of the composition are released. Such a system is described, for example, in U.S. Pat. Publn. No. 20030177784, which is incorporated herein by reference. In some cases, the container comprises foil or similar impermeable material such as a polymer, such that the container may be pressured by effectively dispense liquids or semi-liquids readily.

In a further embodiment, the present disclosure provides a unit dosage of a composition of the embodiments comprised in a gas impermeable container. In certain aspects, the container may be a paste, gel, pill, tablet or a capsule. In another aspect, the container may be a bottle. For example, a container can enclose 1-5 ml; 5-25 ml; 25-100 ml; 125-300 ml; 355-500 ml; 500 ml to 1 liter or more of the composition, such as an emulsion of the embodiments.

In some further embodiments there is provided a method of improving the health or well-being of a subject comprising administering to the subject (or providing the subject with) a composition in accordance the embodiments. For example, the subject can be provided with an amount to of a Noble gas composition of the embodiments that is sufficient to reduce the level of at least one marker of inflammation or cardiovascular risk (e.g., blood pressure). For example, in some cases a Noble gas composition is administered in as an oral liquid or semi-liquid formulation to provide a daily dose equivalent to between about 0.1 to 200 mg/day of Xe. In another example, a daily Xe dose may be between about 1 to 100 mg, 1 to 50 mg, 1 to 25 mg or 1 to 10 mg per day of Xe. In another example, a Noble gas composition is administered as an oral formulation to provide a daily dose equivalent to between about 0.1 to 5 g/day of Xe. For instance, the daily dosage of Xe can be between about 0.1, 0.2, 0.3, 0.4, 0.5, 0.6, 0.7, 0.8, 0.9, or 1.0 and 1.5, 2.0, 2.5, 3.0, 3.5, 4.0, 4.5 or 5.0 grams per day of Xe. In a further embodiment, a method comprises administering an oral Xe composition in a dose of between about 0.1 and 10; 0.1 and 5; 0.5 and 5; 1.0 and 3.0; or 2.0 and 3.0 mg (of Xe)/Kg/day. In still further aspects, a method of the embodiment comprises administering (or providing to a subject) a dose of Noble gas (e.g., Xe) to achieve an initial maximal blood concentration of between 10 μM and 500 μM, between 10 μM and 100 μM, between 10 μM and 50 μM or an initial maximal blood concentration of at least 50 or 100 μM. For example, in some aspects, such a dose of composition of the embodiments is administered daily, every two days, or weekly.

In a further embodiment, the present disclosure provides a method of providing neurological or cardiovascular protection is a subject comprising orally administering an effective amount of a composition in accordance with any one of the embodiments. In certain aspects, the subject (e.g., a human subject) has or is at risk for Alzheimer's disease, thrombotic stroke, ischemic stroke or cardiac hypertrophy. In some aspects, the method further comprises administering about 25-300 ml/day (70-1,350 mg/day, e.g., 100-1,200 mg/day, 200-1000 mg/day, 500-1000 mg/day or 800-1,200 mg/day) to the subject. The composition may be administered weekly, daily, twice a day, three times a day, every six hours, every three hours or hourly. Likewise, a composition may be administered over the period of a week, two weeks, a month or a year. In some aspects, the method is a method for treating or preventing a neurological disease or neurological injury, such as Alzheimer's disease or thrombotic or ischemic stroke. In further aspects, methods are provided for treating or preventing cardiac hypertrophy, or providing protection from myocardial ischemia.

In still a further embodiment, the present disclosure provides a method of reducing beta-amyloid levels in a subject comprising administering an effective amount of xenon or argon to the subject. In certain aspects, the xenon or argon is administered orally in a composition in accordance with any one of the embodiments. In still other aspects, the xenon or argon or other Noble gas are administered via inhalation or injection (e.g., comprised liposomes).

In a related embodiment, the present disclosure provides a method of treating or preventing the progression of Alzheimer's disease in a subject comprising administering an effective amount of xenon or argon or other Noble gas to the subject. In certain aspects, the xenon or argon is administered orally. In other aspects, the xenon or argon or other Noble gas (e.g., He, Ne or Kr) are administered via inhalation or injection. In some aspects, the subject is a subject who is at risk for developing Alzheimer's disease, such as a subject who has or is diagnosed with a genetic predisposition for Alzheimer's disease.

In yet a further embodiment, the present disclosure provides a method of making a composition for oral administration of xenon or argon comprising (a) solubilizing xenon or argon gas in an edible oil by mixing the oil and gas to produce an edible oil comprising soluble xenon or argon gas. In some aspects, the method further comprises (b) emulsifying the edible oil comprising the soluble gas in an aqueous solution (e.g., a solution comprising a detergent or other emulsifier) to produce an emulsion comprising soluble xenon or argon gas. In some aspects, oil and gas are mixed at a pressure of between about 1 atm and 6 atm, 2 atm and 6 atm or 2 atm and 4 atm, at a temperature of between about 0° C. and 37° C. or 0° C. and 25° C. In certain aspects, solubilizing xenon or argon gas in an edible oil comprises saturating or supersaturating the oil with xenon or argon gas. In some aspects, the method further comprises bottling or capturing the oil or emulsion in a gas impermeable container (e.g., a bottle, capsule or pill). For example, the container may be pressurized, such as container pressurized at 2-6 atm. In certain aspects, steps (a)-(b) of the method may be performed under a xenon or argon or other Noble gas atmosphere (e.g., He, Ne or Kr).

In yet a further embodiment there is provided a method of making a substantially aqueous composition comprising a Noble gas comprising: (a) incubating a Noble gas (or a mixture of Noble gases) with a water soluble encapsulating molecule (e.g., a water soluble polymer); and (b) exposing the encapsulated Noble gas to an aqueous solution to produce an aqueous composition comprising the encapsulated Noble gas. In some aspects, step is (a) is performed at a pressure of between about 2 atm and 10 atm (e.g., a pressure between about 2 atm and 8 atm, 2 atm and 5 atm, 2 atm and 4 atm or at a pressure of about 3 atm), at a temperature of between, e.g., about 25° C. or 4° C. and −180° C. (e.g., for a period of at least 1, 2, 3, 4 or more hours) to produce an encapsulated Noble gas. In certain aspects the incubating of step (a) is performed at a temperature of between about 0° C. and −150° C., −20° C. and −150° C., −20° C. and −100° C., −40° C. and −100° C. or at a temperature of about −80° C. and for a period of at least 8 hours, 12 hours, 24 hours, 48 hours or for between 8 hours and three days. In some cases, step (b) comprises exposing the encapsulated Noble gas to an aqueous solution at a pressure of between about 2 atm and 10 atm (e.g., a pressure between about 2 atm and 8 atm, 2 atm and 5 atm, 2 atm and 4 atm or at a pressure of about 3 atm), e.g., at a temperature of between about 20° C. and 1° C. For example, step (b) can occur over a period of at least 1, 2, 3, 4 or more hours. In still further aspects, the exposing of step (b) is performed at a pressure of between about 2 atm and 8 atm, 2 atm and 5 atm, 2 atm and 4 atm or at a pressure of about 3 atm. In some aspects, the exposing of step (b) is performed at a temperature of between about 15° C. and 1° C., 10° C. and 1° C., 8° C. and 2° C., 6° C. and 2° C. or at a temperature of about 4° C. In still further aspects, the exposing of step (b) is for a period of at least 8 hours, 12 hours, 24 hours, 48 hours or for between 8 hours and three days. In still further aspects, the exposing of step (b) comprises exposing the encapsulated Noble gas to an aqueous solution that comprises of is a saturated with a Noble gas or a mixture of Noble gases. For example, the solution can be saturated with a Noble gas by a method comprising: (i) obtaining a degassed aqueous solution; and (ii) exposing the degassed aqueous solution to a Noble gas at a pressure of between about 2 atm and 10 atm, at a temperature of between about 20° C. and 1° C. for at least 4 hours to produce an aqueous solution saturated with the Noble gas.

In yet a further embodiment, the present disclosure provides a composition for use in providing neurological or cardiovascular protection in a subject, the composition comprising edible oil saturated with a Noble gas, such as xenon or argon gas.

In a particular aspect of the embodiments there is provided a method of delivery of a Noble in a substantially aqueous composition comprising supplying a beer, cider, soda or other carbonated beverage from a tap operably coupled to a Noble gas canister (e.g., a Xe gas canister), such that the Noble gas is used to maintain tap pressure and it thereby dissolved into the beverage (e.g., beer) being dispensed from the tap.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A. Intra-ventricular septum in diastole (IVS:d) (mm). FIG. 1B. Left ventricular posterior wall diameter in diastole (LVPW:d) (mm). FIG. 1C. Left ventricular (LV) volume in diastole (LV Vol;d) (μL). $*p<0.05$, $**\ p<0.01$, KO/KO6w compared to WT/WT6w, respectively; $\#p<0.05$, KO control/vehicle compared to KO 6w; $\S\ p<0.05$, $\S\S\ p<0.01$, $\S\S\S\ p<0.001$, KO xenon compared to KO vehicle. WT=Wild type mice; KO=Apo E knockout mice.

FIG. 3A. LV mass corrected (mg). FIG. 3B. Ratio of heart weight (HW) to body weight (BW) (mg/g). WT-6w (n=5): WT mice fed with regular diet for $6^{th}$ week. KO-6w (n=4): the KO mice fed with regular diet for $6^{th}$ week. KO-6w control (n=5): the KO mice fed with high fat diet and administered by PBS gavage for $6^{th}$ week. KO-6w vehicle (n=7): the KO fed with high fat diet and vehicles for $6^{th}$ week. KO-6w Xenon (n=6): the KO fed with high fat diet and administered with Xenon-rich-solution for $6^{th}$ week. $*p<0.05$, KO/KO6w compared to WT/WT6w, respectively; $\S\ p<0.05$, KO6w xenon compared to KO6w vehicle.

FIG. 7A. Infarct size. FIG. 7B. Percent infarct volume. FIG. 7C. Limb placement. FIG. 7D. Grid walking.

FIGS. 13A-13B. Effects of Xe on ischemic stress. Graph in FIG. 13A shows the results of studies to measure CKMB Creatine Kinase (CKMB) levels in the control mice versus Xe-treated animals. Graph in FIG. 13B shows the results of studies to measure troponin expression levels in the control mice versus Xe-treated animals (Mean±SE, n=5, $\S\ p<0.01$).

DESCRIPTION OF ILLUSTRATIVE EMBODIMENTS

Nobel gases such as Xenon (Xe) and Argon (Ar) are attractive since they may improve health and well-being at low dosages and are also potential therapeutics if given at higher dosages. However, there are a wide range of difficulties in attempting to administer such gases to humans. In particular, the amount of gas that can be administered via inhalation is a very serious limitation. Likewise, because these gases are chemically neutral and non-polar formulation into other delivery vehicles has proved to a very difficult challenge.

Figure 14A:
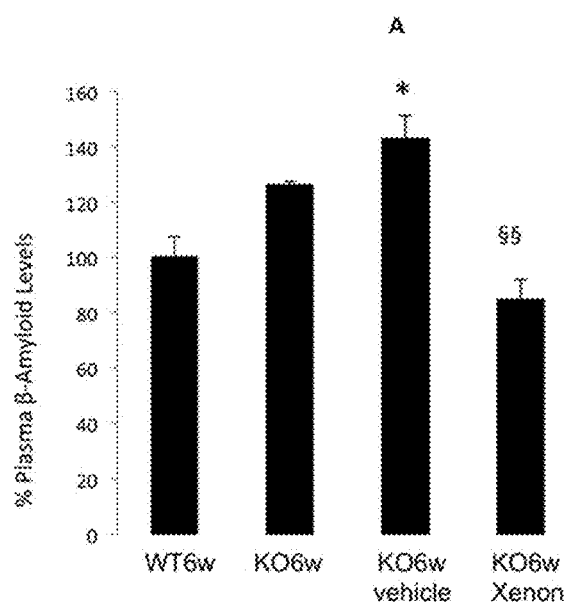
FIGS. 14A-14B. Xe-rich-water decreases expression of β-amyloid in brain and blood. Graphs show the amount of β-amyloid that was found plasma (14A) or brain (14B) after 6 weeks of treatment. WT6w (n=10) indicates mice fed with regular diet at 6th week; KO-6w (n=5) indicates ApoE knock mice fed with regular diet at 6th week; KO6w vehicle (n=7) indicates ApoE knock mice fed with high fat diet and water containing cyclodextrin at 6th week; KO6w Xenon (n=6) indicates ApoE knock mice fed with high fat diet and Xe-rich-Water at 6th week. $*p<0.05$, KO6w vehicle compared to WT6w; $\S\S\ p<0.01$, KO6w Xenon compared to the vehicle.
Figure 14B:
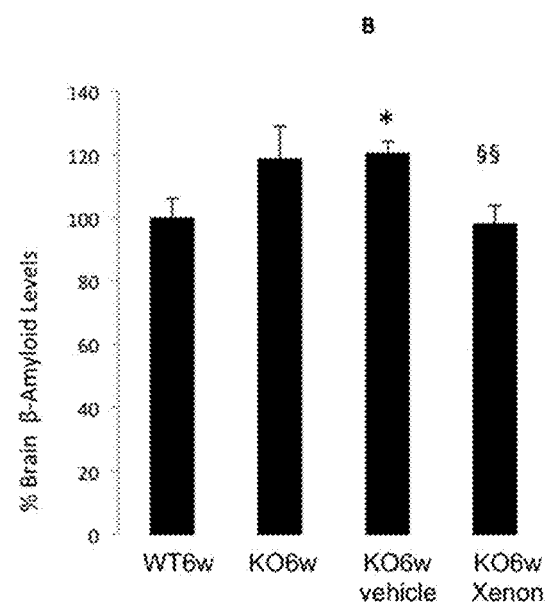

Disclosed herein are solutions rich in a Noble gas, such as Xe or Ar for oral delivery to humans and in some cases other animals of interest. In some aspects, these solutions use lipids including but not limited to oils such as edible oils (e.g., omega-3 rich oils) from known foods as a carrier media to provide increased solubility of such Noble gases. Alternatively or additionally aqueous solutions can incorporate a Noble gas encapsulated in polymer (e.g., cyclodextrin includes: α-cyclodextrin: 6-membered sugar ring molecule, β-cyclodextrin: 7-membered sugar ring molecule, and γ-cyclodextrin: 8-membered sugar ring molecule and various derivatives). Derivatives of cyclodextrins include but are not limited to Methyl-β-cyclodextrin, randomly methylated-β-cyclodextrin, dimethyl-β-cyclodextrin, randomly dimethylated-β-cyclodextrin, Trimethyl-β-cyclodextrin; Acetylated dimethyl-β-cyclodextrin: 2-Hydroxyethyl-β-cyclodextrin, 2-Hydroxypropyl-β-cyclodextrin, 3-Hydroxypropyl-β-cyclodextrin; Hydroxybutenyl-β-cyclodextrin: 2,3-Dihydroxypropyl-β-cyclodextrin, 2-Hydroxypropyl-γ-cyclodextrin; glucosyl-β-cyclodextrin; maltosyl-β-cyclodextrin; glucuronyl-glucosyl-β-cyclodextrin; 2, hydrophobic CD that can be combined with lipid/oil: alkylated β-cyclodextrin, 2,6-Di-O-ethyl-β-cyclodextrin, 2,3,6-Tri-O-ethyl-β-cyclodextrin; acylated β-Cyclodextrin: 2,3,6-Tri-O-acyl($C_2$-$C_{18}$)-β-cyclodextrin, 2,3,6-Tri-O-butanoyl-β-cyclodextrin, 2,3,6-Tri-O-valeryl-β-cyclodextrin, 2,3,6-Tri-O-octyl-β-cyclodextrin, O-Carboxymethyl-O-ethyl-β-cyclodextrin, β-Cyclodextrin sulfate; sulfobutyl ether group-β-cyclodextrin; and sulfobutyl ether group-β-cyclodextrin. Studies herein demonstrate that both types of solutions are able to provide a significant level of Noble gas in an aqueous-based system. Upon oral delivery these solutions have preventive effects in the brain and heart tissues. For example, Xe solutions are shown to increase tolerance of tissues to ischemic damage and provide cardio-protective effects. In model systems for heart disease the compositions are able not only to have a direct positive effect marker of cardiac function (see, e.g., FIGS. 12A-12C) but are also able to lower overall blood pressure in mice deficient for Apo-E (results shown in Table 2). Moreover, these solutions also demonstrate biologically significant (therapeutic) effects in model systems for Alzheimer's disease. In particular, Xe based compositions are shown effective in reducing β-amyloid load in both the blood and brain tissues of treated animals (FIGS. 14A-14B). Thus, compositions are provided comprising effective amounts of dissolved or trapped Ar or Xe that can be used to provide cardiovascular and neuro-protective effects to a subject.

The Noble gas compositions and therapeutic methods disclosed herein offer new avenues for the increasing well-being as well as for the treatment and prevention of a wide range of chronic diseases. Importantly, the compositions provided herein have been shown to provide potent cardio-protective and blood pressure lowering effects at specific dosages that could be useful in treatment of patients with heart disease or who have a high risk of stroke. Likewise, the provided Noble gas compositions are shown able to reduce amyloid load in body tissues and therefore offer a unique therapy to treat and prevent the onset of Alzheimer's disease. Given the convenient aqueous formulations that have now been achieved, effective amounts of non-toxic Noble gases can now be easily delivered via oral formulations. Given the stability of the formulations a variety of doses could be easily distributed without complex packaging, dosing systems or even refrigeration that improve wellbeing by increasing or improving certain physiological parameters (e.g. reducing inflammation, reducing stress, increased, relaxation, reducing blood pressure, clearing the mind) at certain dosages to therapeutic/preventives at other dosages (e.g. improved cardiac and neurological function). Accordingly, a range of compositions intended for primarily oral delivery including but not limited to beverages could be used for gas delivery to provide an effective and convenient nutraceutical or therapeutic that is easily incorporated into standard preventative therapies such as diet modification and exercise. Moreover, because of the ease of delivery and the lack of toxicity formulations, provided here could likely be administered with little or no supervision from medical professionals.

I. Pharmaceutical and Nutraceutical Formulations

Pharmaceutical and nutraceutical compositions provided herein comprise an effective amount of a tissue or cell protective gas, such as Xe or Ar, and, optionally additional agents such as further gases, dissolved or dispersed in an acceptable carrier can be included. In some aspects, such an acceptable carrier includes components formulated to increase or control the content of soluble gas to desired levels, such as lipids including edible oils or caging molecule as detailed above. The Phrase "containing" means the dissolving, emulsifying, suspending, trapping and other like means of obtaining a solution with Nobel gas for primarily oral delivery. The phrase "acceptable carrier" refer to molecular entities and compositions that do not produce an adverse, allergic or other untoward reaction when administered to (e.g., ingested by) an animal, such as, for example, a human, as appropriate. The preparation of a pharmaceutical or nutraceutical composition that contains a Noble gas is detailed herein. Further addition of active or inactive ingredients to such a composition will be known to those of skill in the art in light of the present disclosure, and as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

An "acceptable carrier" may include any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated. In general the carriers of the present embodiments all comprise an oil-based component that comprises a dissolved Noble gas, such as Ar or Xe.

In certain embodiments, the pharmaceutical composition may comprise different types of carriers depending on whether it is to be administered in solid, liquid or aerosol form, and whether it need to be sterile for such routes of administration as injection. In certain embodiments, pharmaceutical compositions provided herein can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, inhalation (e.g. aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

In other embodiments, one may use eye drops, nasal solutions or sprays, aerosols or inhalants in the present embodiments. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in preferred embodiments the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistamines.

Additional formulations which are suitable for other modes of administration include suppositories. Suppositories are solid dosage forms of various weights and shapes, usually medicated, for insertion into the rectum, vagina or urethra. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

Sterile injectable solutions can also be prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area. In particular embodiments, prolonged absorption of an injectable composition can be brought about by the use in the compositions of agents delaying absorption, such as, for example, aluminum monostearate, gelatin or combinations thereof.

The composition must be stable under the conditions of manufacture and storage, and preserved against the contaminating action of microorganisms, such as bacteria and fungi. Where clinical application of liposomes (e.g., liposomes comprising gases) is undertaken, solutions of therapeutic compositions can be prepared in water suitably mixed with a surfactant, such as hydroxypropylcellulose. Dispersions also can be prepared in glycerol, liquid polyethylene glycols, mixtures thereof and in oils. Under ordinary conditions of storage and use, these preparations contain a preservative to prevent the growth of microorganisms. The therapeutic compositions of the present invention are advantageously administered in the form of injectable compositions either as liquid solutions or suspensions; solid forms suitable for solution in, or suspension in, liquid prior to injection may also be prepared. These preparations also may be emulsified. A typical composition for such purpose comprises a pharmaceutically acceptable carrier. For instance, the composition may contain 10 mg, 25 mg, 50 mg or up to about 100 mg of human serum albumin per milliliter of phosphate buffered saline. Other pharmaceutically acceptable carriers include aqueous solutions, non-toxic excipients, including salts, preservatives, buffers and the like.

Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components the pharmaceutical composition are adjusted according to well-known parameters. Additional formulations are suitable for oral administration. Oral formulations include such typical excipients as, for example, pharmaceutical grades of mannitol, lactose, starch, magnesium stearate, sodium saccharine, cellulose, magnesium carbonate and the like. The compositions generally will take the form of solutions or suspensions.

The therapeutic compositions of the present embodiments may include classic pharmaceutical preparations. Administration of therapeutic compositions according to the present invention will be via any common route so long as the target tissue is available via that route. In this case, intravenous injection or infusion may be preferred. Such compositions would normally be administered as pharmaceutically acceptable compositions that include physiologically acceptable carriers, buffers or other excipients.

Oral Formulations

In certain preferred embodiments, a composition of the embodiments is administered orally and is formulated to facilitate such oral administration (e.g., as a beverage formulation). Thus, in some embodiments a composition (such as an emulsion of oil-encapsulated gas or polymer encapsulated gas) may comprise, for example, solutions, suspensions, emulsions, tablets, pills, capsules (e.g., hard or soft shelled gelatin capsules), sustained release formulations, buccal compositions, troches, elixirs, suspensions, syrups, or combinations thereof. Oral compositions may be incorporated directly with a food or drink product (e.g., along with a fruit juice or alcohol). Preferred carriers for oral administration comprise inert diluents, assimilable edible carriers or combinations thereof. In other aspects, the oral composition may be prepared as a syrup or elixir. A syrup or elixir, and may comprise, for example, at least one active agent, a sweetening agent, a preservative, a flavoring agent, a dye, a preservative, or combinations thereof.

In further aspects, a composition comprising dissolved Noble gas, such as Xe or Ar, can be formulated into a capsule or tablet for oral administration. In some aspects, the capsule is substantially impermeable to gas, and preferably the capsule is formulated to dissolve in the gastrointestinal tract of a subject.

In certain preferred embodiments an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof an excipient, such as, for example, dicalcium phosphate, mannitol, lactose, starch, magnesium stearate, sodium saccharine, cellulose, magnesium carbonate or combinations thereof a disintegrating agent, such as, for example, corn starch, potato starch, alginic acid or combinations thereof a lubricant, such as, for example, magnesium stearate; a sweetening agent, such as, for example, sucrose, lactose, saccharin or combinations thereof a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

A composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In embodiments where the composition is in a liquid form, a carrier can comprise a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

Additional Components for Pharmaceutical and Nutraceutical Formulations

Oral Noble gas formulations of the embodiments may comprise additional components as detailed herein below. It is contemplated that such additional components may be included, for example, as at least or at most about 1, 2, 3, 4, 5, 6, 7, 8, 9, 10, 11, 12, 113, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89 or 90% of the total composition on a weight:weight or volume:volume basis. In certain aspects, an additional component comprises less than about 20%, 10%, 5% or less of the total composition on a weight:weight or volume:volume basis.

In some embodiments micronutrients can included, such as (without limitation) L-carnitine, choline, coenzyme Q10, alpha-lipoic acid, omega-3-fatty acids, pepsin, phytase, trypsin, lipases, proteases, cellulases, and a combination comprising at least one of the foregoing micronutrients.

Antioxidants can include materials that scavenge free radicals. In some embodiments, exemplary antioxidants can include citric acid, rosemary oil, vitamin A, vitamin E, vitamin E phosphate, tocopherols, di-alpha-tocopheryl phosphate, tocotrienols, alpha lipoic acid, dihydrolipoic acid, xanthophylls, beta cryptoxanthin, lycopene, lutein, zeaxanthin, astaxanthin, beta-carotene, carotenes, mixed carotenoids, polyphenols, flavonoids, and a combination comprising at least one of the foregoing antioxidants.

Exemplary nutrients can also include amino acids such as L-tryptophan, L-lysine, L-leucine, L-methionine, 2-aminoethanesulfonic acid (taurine), and L-carnitine; creatine; glucuronolactone; inositol; and a combination comprising at least one of the foregoing nutrients.

Phytochemicals ("phytonutrients") are plant derived compounds which may provide a beneficial effect on the health or well-being of the consumer. Phytochemicals include plant derived antioxidants, phenolic compounds including monophenols and polyphenols, and the like. Exemplary phytochemicals include lutein, lycopene, carotene, anthocyanin, capsaicinoids, flavonoids, hydroxycinnamic acids, isoflavones, isothiocyanates, monoterpenes, chalcones, coumestans, dihydroflavonols, flavanoids, flavanols, quercetin, flavanones, flavones, flavan-3-ols (catechins, epicatechin, epigallocatechin, epigallocatechingallate, and the like), flavonals (anthocyanins, cyanidine, and the like); phenolic acids; phytosterols, saponins, terpenes (carotenoids), and a combination comprising at least one of the foregoing phytochemicals.

The phytochemicals can be provided in substantially pure or isolated form or in the form of natural plant extracts. Suitable plant extracts which contain one or more phytochemicals include fruit skin extracts (grape, apple, crab apple, and the like), green tea extracts, white tea extracts, green coffee extract, and a combination comprising at least one of the foregoing extracts.

Various herbals, aromatic plants or plant parts or extracts thereof, can also be included in the compositions for a variety of reasons such as for flavor or for their potential health benefits. Exemplary herbals include *Echinacea*, Goldenseal, Calendula, Rosemary, Thyme, Kava Kava, Aloe, Blood Root, Grapefruit Seed Extract, Black Cohosh, *Ginseng*, Guarana, Cranberry, *Ginko Biloba*, St. John's Wort, Evening Primrose Oil, Yohimbe Bark, Green Tea, Ma Huang, Maca, Bilberry, extracts thereof, and a combination comprising at least one of the foregoing herbals. Additional plant extracts for inclusion in a composition of the embodiments include, but are not limited to, extracts or components from Acai, *Spirulina, Chlorella*, Wheat Grass, Black Soy Bean, Turmeric, Chia Seeds, Coconut Oil, Cocoa, Lingon Berries, Eggs, Beat Juice, Mustard Greens, Sweet Potatoes, Red Wine, Avocados, Blue Berries, Black Berries, Almonds, Green Tea, Lentils, Black Beans and Aloe Vera. For example, in some aspects, a composition of the embodiments includes a protein source selected from the group consisting of whey protein concentrate, potassium caseinate, egg albumin, soy isolate, and whey isolate, (Brown) rice protein, hydrolyzed beef protein isolate, Pea Protein Isolate, and hemp protein.

In still further aspects, a composition of the embodiment can include a diuretic, such a watermelon extract or dandelion leaf extract (e.g., 4:1).

In some embodiments, the composition can have a Brix measurement as measured by a Brix refractometer at 20° C. of about 8.0 to about 9.5° Brix, specifically about 8.5 to about 8.9° Brix. In another embodiment, the composition can have a Brix measurement as measured by a Brix densitometer at 20° C. of about 7.5 to about 9.1° Brix, specifically about 7.9 to about 8.3° Brix.

Electrolytes

The inclusion of electrolytes in the various aspects of the compositions of the invention is contemplated. Exemplary electrolytes include salts of a metal of the groups I and II of the periodic table, preferably the inorganic and organic salts of sodium, potassium, calcium and/or magnesium. Examples of such salts include, but are not limited to, are sodium acetate, acidic sodium citrate, acidic sodium phosphate, sodium amino salicylate, sodium bicarbonate, sodium bromide, sodium chloride, sodium citrate, sodium lactate, sodium phosphate, sodium salicylate, sodium sulphate (anhydrous), sodium sulphate (Glauber's salt), potassium acetate, potassium bicarbonate, potassium bromide, potassium chloride, potassium citrate, potassium-D-gluconate, mono- and dibasic potassium phosphate, calcium acetate, calcium chloride, calcium citrate, calcium-D-gluconate, calcium lactate, calcium laevulinate, dibasic calcium phosphate, magnesium chloride and magnesium sulfate. In one aspect, the electrolytes are sodium chloride, monopotassium phosphate and magnesium sulfate and, when present in an 8 oz. volume, are included in amounts of about 50 mg to about 500 mg, from about 10 mg to about 200 mg and from about 10 mg to about 200 mg, respectively. In other aspects, sodium chloride, when present in an 8 oz. volume, is included in an amount ranging from about 50 mg to about 60 mg, about 70 mg, about 80 mg, about 90 mg or about 100 mg and magnesium sulfate and monopotossium phosphate, when present in an 8 oz. volume, are included in amounts of about 10 mg to about 20 mg, about 30 mg, about 40 mg, about 50 mg, about 60 mg, about 70 mg, about 80 mg, about 90 mg, about 100 mg, or about 200 mg. Compositions of the embodiments can likewise include glycerol.

Additional electrolytes and liquid formulation for composition are provides in U.S. Pat. Nos. 4,981,687, 5,089,477, 5,147,650, 5,236,712, and 5,238,684, each of which are incorporated herein by reference.

Vitamins and Minerals

It is contemplated to include vitamin and/or minerals into various aspects of the compositions of the embodiments. Vitamins for inclusion include, but are not limited to, Vitamins and Co-Vitamins such as Vitamin A (beta-carotene), Choline, Vitamin B1 (thiamin), Vitamin B2 (riboflavin, vitamin G), Vitamin B3 (niacin, vitamin P, vitamin PP), Vitamin B5 (pantothenic acid), Vitamin B6 (pyridoxine, pyridoxamine, or pyridoxal), Vitamin B7 (biotin, vitamin H), Vitamin B9 (folic acid, folate, vitamin M), Vitamin B12 (cobalamin), Vitamin C (ascorbic acid), Vitamin D (ergocalciferol, or cholecalciferol), Vitamin E (tocopherol) and Vitamin K (naphthoquinoids). Minerals for possible inclusion include, without limitation, Calcium (Ca), Chloride (Cl−), Chromium (Cr), Cobalt (Co) (as part of Vitamin B12), Copper (Cu), Iodine (I), Iron (Fe), Magnesium (Mg), Manganese (Mn), Molybdenum (Mo), Phosphorus (P), Potassium (K), Selenium (Se), Sodium (Na) and Zinc (Zn).

Vitamin A, for example, helps in the formation and maintenance of healthy teeth, skeletal and soft tissue, mucous membranes, and skin. It is also known as retinol because it generates the pigments that are necessary for the working of the retina. It promotes good vision, especially in dim light. Beta-carotene is a precursor to vitamin A that has antioxidant properties, helping the body deal with unstable chemicals called free radicals.

Thiamine (B-1) helps the body cells convert carbohydrates into energy. It is also essential for the functioning of the heart and for healthy nerve cells, including those in the brain. Riboflavin (B-2) works with the other B vitamins and is important for body growth and red blood cell production. Similar to thiamine, it helps in releasing energy from carbohydrates. Niacin (B-3) is a B vitamin that helps maintain healthy skin and nerves. It is also important for the conversion of food to energy and may have cholesterol-lowering effects. Vitamin B-6 is also known as pyridoxine and aids in the formation of red blood cells and in the maintenance of normal brain function. It also assists in the synthesizing of antibodies in the immune system. Vitamin B-12, like the other B vitamins, is important for metabolism, participating in, for example, the formation of red blood cells. Pantothenic acid is essential for the metabolism of food. It is also essential in the synthesis of hormones and cholesterol. Biotin is essential for the metabolism of proteins and carbohydrates, and in the synthesis of hormones and cholesterol. Folate (folic acid) works with vitamin B-12 in the production of red blood cells and is necessary for the synthesis of DNA.

Vitamin C, also called ascorbic acid, promotes healthy teeth and gums, helps in the absorption of iron, and helps maintain normal connective tissue. It also promotes wound healing and is an antioxidant.

Vitamin D promotes the body's absorption of calcium, which is essential for the normal development and maintenance of healthy teeth and bones. It also helps maintain adequate blood levels of calcium and phosphorus, which are minerals necessary for many functions.

Vitamin E is also known as tocopherol and is an antioxidant. It is also important in the formation of red blood cells and the use of vitamin K.

Therefore, it is desirable to incorporate various vitamin types into the various aspects of the compositions of the invention. In one embodiment, vitamin B1 (thiamin) when present in an 8 oz. volume, is included in an amount ranging from about 0.1 mg to about 5 mg; vitamin B2 (riboflavin), when present in an 8 oz. volume, is included in an amount ranging from about 0.1 mg to about 5 mg; vitamin B3 (niacin), when present in an 8 oz. volume, is included in an amount ranging from about 1 mg to about 50 mg; vitamin B5 (pantothenoic acid), when present in an 8 oz. volume, is included in an amount ranging from about 1 mg to about 50 mg; vitamin B6, when present in an 8 oz. volume, is included in an amount ranging from about 0.1 mg to about 5 mg; and vitamin B12, when present in an 8 oz. volume, is included in an amount ranging from about 1 μg to about 50 μg. In a further embodiment, vitamins B1, B2 and B6, when present in an 8 oz. volume, are included in amounts of about 0.1 mg to about 2 mg, about 3 mg, about 4 mg, or about 5 mg; vitamins B3 and B5, when present in an 8 oz. volume, are included in amounts of 1 mg, to about 3 mg, about 4 mg, about 5 mg, about 6 mg, about 7 mg, about 8 mg, about 9 mg, about 10 mg, about 20 mg, about 30 mg, about 40 mg, or about 50 mg; and vitamin B12, when present in an 8 oz.

volume, is included in amounts of 1 μg to about 10 μg, about 20 μg, about 30 μg, about 40 μg, or about 50 μg.

In yet another embodiment, a composition of the invention provided further comprising vitamin A, when present in an 8 oz. volume, is included in an amount ranging from about 50 IU to about 1000 IU. In one aspect, vitamin A, when present in an 8 oz. volume, is included in amounts of about 50 IU to about 100 IU, about 200 IU, about 300 IU, about 400 IU, about 500 IU, about 600 IU, about 700 IU, about 800 IU, about 900 IU or about 1000 IU.

In another embodiment, a composition of the embodiments is provided further comprising, vitamin C, when present in an 8 oz. volume, is included in an amount ranging from about 10 mg to about 100 mg. In some aspects, vitamin C, when present in an 8 oz. volume, is included in amounts of 10 mg to about 20 mg, about 30 mg, about 40 mg, about 50 mg, about 60 mg, about 70 mg, about 80 mg, about 90 mg, or about 100 mg.

In yet another embodiment, a composition of the invention is provided further comprising vitamin E, when present in an 8 oz. volume, is included in an amount ranging from about 1 IU to about 50 IU. In aspect, vitamin E, when present in an 8 oz. volume, is included in amounts of about 1 IU to about 10 IU, about 20 IU, about 30 IU, about 40 IU, or about 50 IU.

Amino Acids

In a further embodiment, the aforementioned composition is provided further comprising one or more amino acids selected from the group consisting of alanine, arginine, creatine, cysteine, glysine, histidine, glutamine, lysine, methionine, ornithine, leucine, isoleucine, serine, tyrosine, aspartagine, aspartic acid, threonine, proline, tryptophan, valine, phenylalanine, and selenocysteine. For example, creatine can be supplied in its various forms such as creatine monohydrate, creatine magnesium chelate or creatine nitrate.

For example, glutamine, when present in an 8 oz. volume, is included in an amount ranging from about 5 mg to about 100 mg or in amounts of about 5 mg to about 20 mg, about 30 mg, about 40 mg, about 50 mg, about 60 mg, about 70 mg, about 80 mg, about 90 mg or about 100 mg.

Furthermore, the inclusion of cysteine in a composition of the invention is contemplated. For example, cysteine, when present in an 8 oz. volume, is included in an amount ranging from about 10 mg to about 100 mg.

Carbohydrates

As mentioned supra, in some aspects including a carbohydrate source in the composition of the invention is contemplated. Exemplary carbohydrates include, but are not limited to, monosaccharides, a disaccharides, oligosaccharides and a glucose polymers. Modified carbohydrates, such as sucralose, are also contemplated. In another aspect, carbohydrate of the formulation is derived from citric acid.

Flavoring Agents

One or more flavoring agents may be added to the compositions of the invention in order to enhance their palatability. Any natural or synthetic flavor agent can be used in the present invention. For example, one or more botanical and/or fruit flavors may be utilized herein. As used herein, such flavors may be synthetic or natural flavors.

Exemplary fruit flavors include exotic and lactonic flavors such as, for example, passion fruit flavors, mango flavors, pineapple flavors, cupuacu flavors, guava flavors, cocoa flavors, papaya flavors, peach flavors, and apricot flavors. Besides these flavors, a variety of other fruit flavors can be utilized such as, for example, apple flavors, citrus flavors, grape flavors, raspberry flavors, cranberry flavors, cherry flavors, grapefruit flavors, and the like. These fruit flavors can be derived from natural sources such as fruit juices and flavor oils, or may alternatively be synthetically prepared.

Exemplary botanical flavors include, for example, tea (e.g., black and green tea), aloe vera, guarana, *ginseng*, ginkgo, hawthorn, hibiscus, rose hips, chamomile, peppermint, fennel, ginger, licorice, lotus seed, schizandra, saw palmetto, sarsaparilla, safflower, St. John's Wort, *curcuma*, cardimom, nutmeg, *cassia* bark, buchu, cinnamon, jasmine, haw, *chrysanthemum*, water chestnut, sugar cane, lychee, bamboo shoots, vanilla, coffee, and the like.

The flavor agent can also comprise a blend of various flavors. If desired, the flavor in the flavoring agent may be formed into emulsion droplets which are then dispersed in the beverage composition or concentrate. Because these droplets usually have a specific gravity less than that of water and would therefore form a separate phase, weighting agents (which can also act as clouding agents) can be used to keep the emulsion droplets dispersed in the beverage composition or concentrate. Examples of such weighting agents are brominated vegetable oils (BVO) and resin esters, in particular the ester gums. See L. F. Green, Developments in Soft Drinks Technology, Vol. 1, Applied Science Publishers Ltd., pp. 87-93 (1978) (Incorporated herein by reference) for a further description of the use of weighting and clouding agents in liquid beverages. Typically the flavoring agents are conventionally available as concentrates or extracts or in the form of synthetically produced flavoring esters, alcohols, aldehydes, terpenes, sesquiterpenes, and the like.

The amount of flavor agent used will vary, depending on the agents used and the intensity desired in the finished product. The amount can be readily determined by one skilled in the art. Generally, if utilized, the flavor agent should be present at a level of from about 0.0001% to about 0.5%.

Flavanols

Flavanols are natural substances present in a variety of plants (e.g., fruits, vegetables, and flowers). The flavanols which may be utilized in the present invention can be extracted from, for example, fruit, vegetables, green tea or other natural sources by any suitable method well known to those skilled in the art. Flavanols may be extracted from either a single plant or mixtures of plants. Plants containing flavanols are known to those skilled in the art.

The amount of flavanols in the various aspect of the compositions of the invention can vary. However, wherein one or more flavanols are utilized, preferably from about 0.001% to about 5% by weight of the composition.

Sensate Formulations

In some aspects, compositions include "sensates", trigeminal nerve stimulants which can alter the taste of e.g., a beverage composition and decrease the perception of off-notes. Sensates include "warming agents", compounds which provide a sensation of warmth; "cooling agents", compounds which provide a cooling sensation; and "tingling agents", compounds which provide a tingling, stinging or numbing sensation. The sensate may be a warming, a cooling, a tingling agent, or any combination comprising at least one of the foregoing sensates.

Warming agents may be selected from a wide variety of compounds known to provide the sensory signal of warming to the individual user. These compounds offer the perceived sensation of warmth, particularly in the oral cavity, and often enhance the perception of flavors, sweeteners and other organoleptic components. Useful warming agents include those having at least one allyl vinyl component, which may bind to oral receptors. Examples of suitable warming agents include vanillyl alcohol n-butyl ether (TK-1000, supplied by Takasago Perfumery Company Ltd., Tokyo, Japan); vanillyl alcohol n-propyl ether; vanillyl alcohol isopropyl ether; vanillyl alcohol isobutyl ether; vanillyl alcohol n-amino ether; vanillyl alcohol isoamylether; vanillyl alcohol n-hexyl ether; vanillyl alcohol methyl ether; vanillyl alcohol ethylether; gingerol; shogaol; paradol; zingerone; capsaicin; dihydrocapsaicin; nordihydrocapsaicin; homocapsaicin; homodihydrocapsaicin; ethanol; isopropyl alcohol; iso-amyl alcohol; benzyl alcohol; glycerine; chloroform; eugenol; cinnamon oil; cinnamic aldehyde; phosphate derivatives thereof, and the like, or a combination comprising at least one of the foregoing warming sensates.

A variety of well-known cooling agents may be employed in instant compositions. Exemplary cooling agents include menthol, xylitol, erythritol, menthane, menthone, menthyl acetate, menthyl salicylate, N,2,3-trimethyl-2-isopropyl butanamide (WS-23), N-ethyl-p-menthane-3-carboxamide (WS-3), menthyl succinate, 3,1-menthoxypropane 1,2-diol and glutarate esters, among others, and the like, or a combination comprising at least one of the foregoing cooling sensates.

Tingling agents may be employed in the beverage compositions to provide a tingling, stinging or numbing sensation to the user. Exemplary tingling agents include Jambu Oleoresin or para cress (*Spilanthes* sp.), in which the active ingredient is Spilanthol; Japanese pepper extract (*Zanthoxylum peperitum*), including the ingredients known as Saanshool-I, Saanshool-II and Sanshoamide; black pepper extract (*Piper nigrum*), including the active ingredients chavicine and piperine; *Echinacea* extract; Northern Prickly Ash extract; red pepper oleoresin; and the like, or a combination comprising at least one of the foregoing tingling sensates.

A sensate may be present in a composition, such as a composition (e.g., a beverage composition), in an amount of about 0.01 to about 10 weight percent, specifically about 0.1 to about 5.0, and yet more specifically about 1.0 to about 3.0 weight percent based on the total weight of the beverage composition.

Stimulants

In some aspects, a composition of the embodiments includes a stimulant or an agent that provides a feeling of enhanced energy level. For example, a composition can include Caffeine (anhydrous), Green Tea Extract (*Camellia sinensis*) (leaf, e.g., 45% EGCG), *Hoodia gordonii*, Advantra Z® (*Citrus aurantium*, e.g., 60% synephrine alkaloids), L-Taurine, *Panax Ginseng* Powder, Glucuronolactone, Adenosine, Octopamine, L-Carnitine, Yohimbine, Vinpocetine, NADH, Evodiamine Cinnulin PF® Cinnamon Bark Extract (*Cinnamonum burmannii*), Banaba Leaf Extract, or Zychrome® [Chromium (as Chromium Dinicocysteinate).

Coloring Agent

Small amounts of one or more coloring agents may be utilized in the compositions of the present invention. FD&C dyes (e.g., yellow #5, blue #2, red #40) and/or FD&C lakes are preferably used. By adding the lakes to the other powdered ingredients, all the particles, in particular the colored iron compound, are completely and uniformly colored and a uniformly colored beverage mix is attained. Preferred lake dyes which may be used in the present invention are the FDA-approved Lake, such as Lake red #40, yellow #6, blue #1, and the like. Additionally, a mixture of FD&C dyes or a FD&C lake dye in combination with other conventional food and food colorants may be used. Riboflavin and b-carotene may also be used. Additionally, other natural coloring agents may be utilized including, for example, fruit, vegetable, and/or plant extracts such as grape, black currant, *Aronia*, carrot, beetroot, red cabbage, and hibiscus.

The amount of coloring agent used will vary, depending on the agents used and the intensity desired in the finished product. The amount can be readily determined by one skilled in the art. Generally, if utilized, the coloring agent should be present at a level of from about 0.0001% to about 0.5%, preferably from about 0.001% to about 0.1%, and most preferably from about 0.004% to about 0.1%, by weight of the composition.

Preservatives

Preservatives may or may not be needed for use in the present compositions. Techniques such as aseptic and/or clean-fill processing may be utilized to avoid preservatives. One or more preservatives may, however, optionally be added to the present compositions. Preferred preservatives include, for example, sorbate, benzoate, and polyphosphate preservatives (for example, sodium hexametapolyphosphate).

Preferably, wherein a preservative is utilized herein, one or more sorbate or benzoate preservatives (or mixtures thereof) are utilized. Sorbate and benzoate preservatives suitable for use in the present invention include sorbic acid, benzoic acid, and salts thereof, including (but not limited to) calcium sorbate, sodium sorbate, potassium sorbate, calcium benzoate, sodium benzoate, potassium benzoate, and mixtures thereof.

Wherein a composition comprises a preservative, the preservative is preferably included at levels from about 0.0005% to about 0.5%, more preferably from about 0.001% to about 0.4% of the preservative, still more preferably from about 0.001% to about 0.1%, even more preferably from about 0.001% to about 0.05%, and most preferably from about 0.003% to about 0.03% of the preservative, by weight of the composition. Wherein the composition comprises a mixture of one or more preservatives, the total concentration of such preservatives is preferably maintained within these ranges.

Acidulants

If desired, the present compositions may optionally comprise one or more acidulants. An amount of an acidulant may be used to maintain the pH of the composition. Compositions of the present invention, in various aspects, have a pH of from about 2 to about 9, from about 2.5 to about 8.5, from about 3 to about 8, from about 03.5 to about 7.5, from about 4 to about 7, from about 4.5 to about 6.5, or from about 5 to about 6.

Acidity of a composition can be adjusted to and maintained within the requisite range by known and conventional methods, e.g., the use of one or more of the aforementioned acidulants. Typically, acidity within the above recited ranges is a balance between maximum acidity for microbial inhibition and optimum acidity for the desired beverage flavor.

Organic as well as inorganic edible acids may be used to adjust the pH of the beverage, and may be added additional to the acid serving as part of the second component herein. The acids can be present in their undissociated form or, alternatively, as their respective salts, for example, potassium or sodium hydrogen phosphate, potassium or sodium dihydrogen phosphate salts. The preferred acids are edible organic acids which include citric acid, malic acid, fumaric acid, adipic acid, phosphoric acid, gluconic acid, tartaric acid, ascorbic acid, acetic acid, phosphoric acid or mixtures thereof. The most preferred acids are citric and malic acids.

The acidulant can also serve as an antioxidant to stabilize beverage components. Examples of commonly used antioxidant include but are not limited to ascorbic acid, EDTA (ethylenediaminetetraacetic acid), and salts thereof.

The amount of acidulant used will vary, depending on the agent used and the pH desired in the finished product. The amount can be readily determined by one skilled in the art. Generally, if utilized, the acidulant should be present at a level of from about 0.0001% to about 0.5% by weight of composition.

Antioxidants

A composition of the embodiment may, in some aspects, further comprise an antioxidant. For example, the antioxidant may be natural or synthetic. Suitable antioxidants include, but are not limited to, ascorbic acid and its salts, ascorbyl palmitate, ascorbyl stearate, anoxomer, N-acetylcysteine, benzyl isothiocyanate, o-, m- or p-amino benzoic acid (o is anthranilic acid, p is PABA), butylated hydroxyanisole (BHA), butylated hydroxytoluene (BHT), caffeic acid, canthaxantin, alpha-carotene, beta-carotene, beta-carotene, beta-apo-carotenoic acid, carnosol, carvacrol, cetyl gallate, chlorogenic acid, citric acid and its salts, clove extract, coffee bean extract, p-coumaric acid, 3,4-dihydroxybenzoic acid, N,N'-diphenyl-p-phenylenediamine (DPPD), dilauryl thiodipropionate, distearyl thiodipropionate, 2,6-di-tert-butylphenol, dodecyl gallate, edetic acid, ellagic acid, erythorbic acid, sodium erythorbate, esculetin, esculin, 6-ethoxy-1,2-dihydro-2,2,4-trimethylquinoline, ethyl gallate, ethyl maltol, ethylenediaminetetraacetic acid (EDTA), *Eucalyptus* extract, eugenol, ferulic acid, flavonoids (e.g., catechin, epicatechin, epicatechin gallate, epigallocatechin (EGC), epigallocatechin gallate (EGCG), polyphenol epigallocatechin-3-gallate), flavones (e.g., apigenin, chrysin, luteolin), flavonols (e.g., datiscetin, myricetin, daemfero), flavanones, fraxetin, fumaric acid, gallic acid, gentian extract, gluconic acid, glycine, gum guaiacum, hesperetin, alpha-hydroxybenzyl phosphinic acid, hydroxycinammic acid, hydroxyglutaric acid, hydroquinone, N-hydroxysuccinic acid, hydroxytryrosol, hydroxyurea, lactic acid and its salts, lecithin, lecithin citrate; R-alpha-lipoic acid, lutein, lycopene, malic acid, maltol, 5-methoxy tryptamine, methyl gallate, monoglyceride citrate; monoisopropyl citrate; morin, beta-naphthoflavone, nordihydroguaiaretic acid (NDGA), octyl gallate, oxalic acid, palmityl citrate, phenothiazine, phosphatidylcholine, phosphoric acid, phosphates, phytic acid, phytylubichromel, pimento extract, propyl gallate, polyphosphates, quercetin, trans-resveratrol rice bran extract, rosemary extract, rosmarinic acid, sage extract, sesamol, silymarin, sinapic acid, succinic acid, stearyl citrate, syringic acid, tartaric acid, thymol, tocopherols (i.e., alpha-, beta-, gamma- and delta-tocopherol), tocotrienols (i.e., alpha-, beta-, gamma- and delta-tocotrienols), tyrosol, vanilic acid, 2,6-di-tert-butyl-4-hydroxymethylphenol (i.e., Ionox 100), 2,4-(tris-3',5'-bi-tert-butyl-4'-hydroxybenzyl)-mesitylene (i.e., Ionox 330), 2,4,5-trihydroxybutyrophenone, ubiquinone, tertiary butyl hydroquinone (TBHQ), thiodipropionic acid, trihydroxy butyrophenone, tryptamine, tyramine, uric acid, vitamin K and derivates, resveratrol, CoQ-10 (coenzyme Q10), vitamin C, vitamin E, beta-carotene, other related carotenoids, selenium, manganese, glutathione, lipoic acid, flavonoids, phenols, polyphenols, phytoestrogens, N-Acetyl Cysteine, wheat germ oil, zeaxanthin, or combinations thereof. Preferred antioxidants include tocopherols, ascorbyl palmitate, ascorbic acid, and rosemary extract. The concentration of the additional antioxidant or combination of antioxidants may range from about 0.001% to about 5% by weight, and preferably from about 0.01% to about 1% by weight.

Water

The compositions of the invention may comprise from 0% to about 99.999% water, by weight of the composition. The compositions may comprise at least about 4% water, at least about 20% water, at least about 40% water, at least about 50% water, at least about 75% water, and at least about 80% water. The water included at these levels includes all added water and any water present in combination components, for example, fruit juice.

In various embodiments, the composition is provided in an 1 oz volume, about 2 oz, about 3 oz, about 4 oz, about 5 oz, about 6 oz, about 7 oz, about 8 oz, about 9 oz, about 10 oz, about 12 oz, about 14 oz, about 16 oz, about 18 oz, about 20 oz, about 22 oz, about 24 oz, about 30 oz, or about 40 oz volume or in that volume of water. In one aspect, a water component of the formulation is demineralized water.

Alcohol

In some aspects, a beverage composition of the embodiments includes ethanol, such as between about 1% to 60% alcohol (ABV), or about 1 to 40% alcohol (ABV), or about 1% to 20% alcohol (ABV), or about 1% to 10% alcohol (ABV) (alcohol by volume, ABV). For example, the composition may include distilled spirits, e.g. vodka, rum, whiskey, gin, bourbon, rye, or other sweetened or unsweetened distilled liquors. In some aspects, the beverage may be composed of substantial amount of beer, wine, cider or malt liquor.

Sea Minerals

In some aspects, compositions of the embodiments further comprise sea minerals. Sea minerals are nature's perfect balance of macrominerals, microminerals, and ultra trace minerals. They are present in the most readily assimilated and bio-available form known. Sea mineral levels are almost identical to the mineral levels found in human blood serum and are in pH balance very similar to human blood. Sea minerals are free of toxic heavy metals, such as arsenic, cadmium, mercury, lead, radon, ruthenium, and uranium.

Sea salt, for example, is primarily composed of the following ions, listed in order of descending abundance by weight: Chloride ($Cl^-$) 55.03% Sodium ($Na^+$) 30.59% Sulfate ($SO_4^{2-}$) 7.68% Magnesium ($Mg^{2+}$) 3.68% Calcium ($Ca^{2+}$) 1.18% Potassium ($K^+$) 1.11% Bicarbonate ($HCO_3^-$) 0.41% Bromide ($Br^-$) 0.19% Borate ($BO_3^{3-}$) 0.08% Strontium ($Sr^{2+}$) 0.04% other ions 0.01%. Sea salt allows liquids to freely cross body membranes, e.g.: the glomeruli of the kidney or blood vessel walls. Sea salt is necessary for the proper breakdown of plant carbohydrates into usable and assimilable nutrients.

Lipid Components

As further detailed below compositions of the embodiments may further comprise a lipid component alone or as part of an oil (such as a lipid component that comprises dissolved Noble gas). Lipids for inclusion in compositions of the embodiments include, but are not limited to ω-3 fatty acids such as α-linolenic acid (ALA, 18:3), eicosapentaenoic acid or EPA (20:5n-3), docosahexaenoic acid or DHA (22:6n-3); w-6 fatty acids such as linoleic acid or (LA, 18:2), an omega-6 fatty acid, gamma-linolenic acid or GLA (18:3n-6), dihomo-gamma-linolenic acid or DGLA (20:3n-6) or arachidonic acid or AA (20:4n-6) or w-9 fatty acids. For example, polyunsaturated oils can be derived from Walnuts, Canola Oil, Sunflower Seeds, Sesame Seeds, Chia Seeds, Peanuts, Peanut Butter, Olive Oil, Seaweed, Sardines, Soybeans, Tuna, Wild Salmon or a Whole Grain Wheat, any of which may be used in a composition of the embodiments.

II. Dosing for Noble Gas Formulations

The amount of a Noble gas incorporated into the compositions of the embodiments depend upon the specific formulation used and its intended use. An effective amount of the composition is determined based on the intended goal, such to provide neuro- or cardiovascular protective effect or to provide and improve feeling of well-being to a subject (e.g., reduce inflammation, stress and/or blood pressure). The term "unit dose" or "dosage" refers to physically discrete units suitable for use in a subject, each unit containing a predetermined-quantity of the composition calculated to produce the desired effect. The quantity of a composition to be administered will also depend, both on the frequency of administration and unit dose, depends on the protection desired.

In certain embodiments, the actual dosage amount of a composition provided to a subject can be determined by physical and physiological factors such as body weight, health condition, previous or concurrent therapeutic interventions, diet, and on the route of administration.

An effective dose range of a nutraceutical or therapeutic can be extrapolated, for example, from effective doses determined in animal studies. In general a human equivalent dose (HED) in mg/kg can be calculated in accordance with the following formula (see, e.g., Reagan-Shaw et al., *FASEB J.*, 22(3):659-661, 2008, which is incorporated herein by reference):

$$\text{HED (mg/kg)} = \text{Animal dose (mg/kg)} \times (\text{Animal } K_m/\text{Human } K_m)$$

Use of the $K_m$ factors in conversion results in more accurate HED values, which are based on body surface area (BSA) rather than only on body mass. $K_m$ values for humans and various animals are well known. For example, the $K_m$ for an average 60 kg human (with a BSA of 1.6 m$^2$) is 37, whereas a 20 kg child (BSA 0.8 m$^2$) would have a $K_m$ of 25. $K_m$ for some relevant animal models are also well known, including: mice $K_m$ of 3 (given a weight of 0.02 kg and BSA of 0.007); hamster $K_m$ of 5 (given a weight of 0.08 kg and BSA of 0.02); rat $K_m$ of 6 (given a weight of 0.15 kg and BSA of 0.025) and monkey $K_m$ of 12 (given a weight of 3 kg and BSA of 0.24).

For example, in a mouse system it is possible to administer between about 200 µl to 5 ml of orally ingested aqueous solution saturated with Xe per day (i.e., about 0.12-3.0 mg/day or about 7.2 to about 180 mg/$\kappa_g$/day for a mouse). Thus, for a human subject that would translate to a dosage of about 500 µg/kg/day to about 12.2 mg/kg/day or for a human of average mass (60 kg) that would be about 30 to about 732 mg/day.

As noted above, the precise amounts of an active gas component depend on the particular formulation. Nonetheless, a calculated HED dose can provide a general guide for dosing that may provide beneficial effects. For the instant embodiments, it is envisioned that the amount of gas, such as Xenon, to be provided in a unit dosage would be from about 0.1 to about 200 mg, considering application of 1-2 doses a day to a an average subject. For example, one ~6 oz. cold bottle of aqueous Xe drink (e.g., comprising cyclodextrin encapsulated Xe) could comprise 4 grams of Xe, while 2 ml of Xe in water at room temperature and 1 atm pressure would comprise 1.2 mg of Xe. In general, oil formulations of Xe can comprise about 20 times more Xe than water (without an encapsulation system. For example, at room temperature and 1 atm, solutions of about 12 mg Xe/ml could be achieved in an oil, such as olive oil.

III. Noble Gas Encapsulation

Oil Components

Certain aspects of the embodiments concern oils that comprise dissolved gases, such as, Ar or Xe. In some aspects the oil is a flaxseed oil, rapeseed oil, soybean oil, walnut oil, fish oil, safflower oil, sunflower oil, avocado oil, coconut oil, corn oil, cotton seed oil, peanut oil, palm oil, olive oil, chia oil, echium oil, krill oil or vegetable oil. In further aspects, the oil is a mixture of two or more oils. It will be understood by the skilled artisan that the oil is preferable an edible, substantially non-toxic oil. Thus, in some aspects, the oil is a non-petroleum based oil, such as an animal or vegetable-derived oil. Preferably the oil comprises a high concentration of omega-3 omega-6- and/or omega-9-fatty fatty acids (e.g., eicosapentaenoic acid, docosahexaenoic acid, stearidonic acid, and/or linolenic acid). In still further aspects, an oil is selected for its concentration of polyunsaturated fatty acids (PUFA), such as oil having at least about 5%, 10%, 20% or more PUFA content.

In certain aspects, oil compositions or emulsions of the embodiments comprise one or more phospholipid component. Phospholipids include, for example, phosphatidylcholines, phosphatidylglycerols, phosphatidylethanolamines glycerophospholipids and certain sphingolipids. Thus, phospholipids for use herein include, but are not limited to, dioleoylphosphatidylycholine ("DOPC"), egg phosphatidylcholine ("EPC"), dilauryloylphosphatidylcholine ("DLPC"), dimyristoylphosphatidylcholine ("DMPC"), dipalmitoylphosphatidylcholine ("DPPC"), di stearoylphosphatidylcholine ("DSPC"), 1-myristoyl-2-palmitoyl phosphatidylcholine ("MPPC"), 1-palmitoyl-2-myristoyl phosphatidylcholine ("PMPC"), 1-palmitoyl-2-stearoyl phosphatidylcholine ("PSPC"), 1-stearoyl-2-palmitoyl phosphatidylcholine ("SPPC"), dilauryloylphosphatidylglycerol ("DLPG"), dimyristoylphosphatidylglycerol ("DMPG"), dipalmitoylphosphatidylglycerol ("DPPG"), di stearoylphosphatidylglycerol ("DSPG"), di stearoyl sphingomyelin ("DS SP"), di stearoylphophatidylethanolamine ("DSPE"), dioleoylphosphatidylglycerol ("DOPG"), dimyristoyl phosphatidic acid ("DMPA"), dipalmitoyl phosphatidic acid ("DPPA"), dimyristoyl phosphatidylethanolamine ("DMPE"), dipalmitoyl phosphatidylethanolamine ("DPPE"), dimyristoyl phosphatidylserine ("DMPS"), dipalmitoyl phosphatidylserine ("DPPS"), brain phosphatidylserine ("BPS"), brain sphingomyelin ("BSP"), dipalmitoyl sphingomyelin ("DPSP"), dimyristyl phosphatidylcholine ("DMPC"), 1,2-distearoyl-sn-glycero-3-phosphocholine ("DAPC"), 1,2-diarachidoyl-sn-glycero-3-phosphocholine ("DBPC"), 1,2-dieicosenoyl-sn-glycero-3-phosphocholine ("DEPC"), dioleoylphosphatidylethanolamine ("DOPE"), palmitoyloeoyl phosphatidylcholine ("POPC"), palmitoyloeoyl phosphatidylethanolamine ("POPE"), lysophosphatidylcholine, lysophosphatidylethanolamine, and dilinoleoylphosphatidylcholine.

In addition to solublization of Noble gases in lipid components (e.g., for emulsification) it is also contemplated that such gases can be provided in an aqueous formulation encapsulated in a liposome. Such liposome encapsulation of gas has been previously demonstrated, see, e.g., U.S. Pat. No. 7,976,743, incorporated herein by reference.

Water Soluble Molecules

As detailed further herein, in certain aspects, Noble gas solubility in an aqueous component is enhanced by encapsulating the gas (gases) in a water soluble molecule such as polymer. In general the molecule used for encapsulation will be a molecule that can form a pocket with increased hydrophobicity that is configured so encompass (at portion of) a Noble gas atom. Such an encapsulating molecule thereby shields the hydrophobic atom from the surrounding polar environment of the aqueous component thereby effectively increasing the content of Noble gas that can be solubilized in the aqueous component.

For example, as shown herein cyclodextrin and its derivatives are well-adapted for encapsulating Noble gas. In the case of the large Xe atom, β-cyclodextrin was used to encapsulate Xe (see, e.g., FIG. 10B). Theoretically, one skilled in the art could increase the concentration of cyclodextrin or Hydroxypropyl-beta-cyclodextrin (hp-beta-CD) or other derivatives to increase the amount of included Xe (i.e. molecular caged Xe). An acceptably safe dose for cyclodextrin can be about 1,000 mg/kg/day for chronic oral administration. Solubility of hp-beta-CD, for example, is 330 mg/ml. That means one can increase cyclodextrin concentration significantly to about 0.5 mg/ml by use of soluble derivatives (See Example 3 and 4). This will be able to bring dissolved gas concentration to at least 500 mg/ml. Additional molecules that are contemplated for gas encapsulation include, without limitation, carcer and or hemicarcerands (see, Saleh 2007), macroglobulin, cucurbituril (see, US 20030140787, incorporated herein by reference), calixarenes (Adams et al., 2008), pillararenes (Cao et al., 2009), prophyrins, metallacrowns, crown ethers, cyclotriveratrylenes, crypotophenes, foldamers, additional cyclodextrin polymers, silsesquioxanes (Skelton et al., 2013), tenas porous polymer, HayeSep® Porous Polymer and Porapak™ Porous Polymer (reach of the foregoing citations incorporated herein by reference). Selection of the particular polymer for encapsulation will depend not only on the Noble gas to be encapsulated, but also the particular type of formulation to be made (e.g., an oral formulation).

IV. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Methods for Studies of Example 2

Preparation of Xe-Rich-Solution.

Xenon-rich-solution was composed of olive oil (or can be made with other oils such as flaxseed oil, rapeseed oil, soybean oil, walnut oil, fish oil etc), egg phosphocholine (Avanti, polar lipid. Alabama, USA), BSA (or other protein such as milk), and lithocholic acid (Sigma-Aldrich, St. Louis, Mo., USA) The solution, comprising 25% oil component, was emulsified using a sonication method and stabled by fabrication of the emulsion with surfactants such as phospholipids (egg PC, soybean PC, DPPC, DOPC etc), proteins and lithocholic acid. Xenon (Matheson Tri-Gas®, Houston, Tex., USA) was saturated into oil by pressurization at low temperature.

Murine Experiment Setting.

Figure 8:
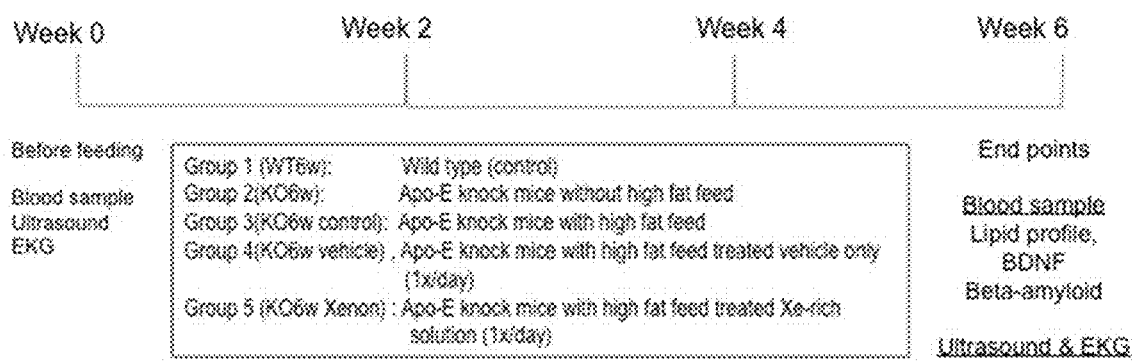
FIG. 8. Example of the exemplary mouse experimental protocol.

All animal studies were approved by the Animal Welfare Committee at The University of Texas Health Science Center at Houston. C57BL/6J wild type (WT) and apolipoprotein-E (Apo E) knockout (KO) mice were purchased from Jackson Laboratory (Bar Harbor, Me., USA), see, e.g., Meir et al., 2004, incorporated herein by reference. The control WT mice used were C57BL/6J, which share the same genetic background with the Apo E KO mice. Six- to eight-month-old male WT and KO mice were fed control or high fat diet (Harlan Laboratories, USA) and administered control or Xe-rich solution (200 μl, once a day) and water drink for 6 weeks, since the Apo E KO mice type fed a high fat diet develop atherosclerotic lesions. See FIG. 8.

Echocardiographic Measurements and Electrocardiographic Images (in Vivo).

Baseline measurements by echocardiography were obtained before feeding with the high fat diet. Cardiac morphology and function were assessed by serial M-mode echocardiography using a Vevo 770 Imaging System (VisualSonics Inc., Ontario, Canada) equipped with a 30 MHz microprobe. M-mode ventricular measurements were taken at 6-weeks after the feeding. Electrocardiographic (ECG) data was obtained. Echo data (HR, heart rate; LVID, left ventricular internal dimension; IVS, intra-ventricular septum; LVPW, left ventricular posterior wall; FS, fractional shortening; SV, stroke volume; EF, ejection fraction; CO, cardiac output; LV Vol, LV volume; LV mass corrected) were analyzed with the analysis software (VisualSonics Inc., Ontario, Canada).

Protein Assays.

Fresh frozen heart and brain tissues were slightly thawed on crushed ice to allow dissection of the hearts and brains. Tissue samples were homogenized by sonicating for 2-3 bursts of 20 seconds on ice using a minimal volume of radioimmunoprecipitation assay (RIPA) buffer (Cell Signaling Technology, Inc., MA, USA) containing protease inhibitors (complete protease inhibitor cocktail, Sigma) and centrifuged for 10 min at 4° C. at 14,000×g. The supernatant was removed. The protein concentration was determined using a Bradford Protein Assay (Bio-Rad, Calif., USA).

Brain-derived Neurotrophic Factor (BDNF) and β-Amyloid Measurements.

Except for the heart and brain extracts, the samples (such as plasma) were thawed and clarified at 12,000 rpm for 10 min at 4° C. prior to ELISA assays for β-amyloid per the manufacturer's instructions. BDNF and β-amyloid peptide (Aβ1-40) content were determined by using BDNF Sandwich ELISA Kit (Millipore Corporation, MA, USA) and a Mouse/Rat Amyloid β (1-40) High Specific ELISA Assay Kit (IBLAmerican, Minneapolis, Minn., USA). Following instructions, the samples were added in the pre-coated 96-well microtiter plates for incubation overnight at 4° C. After washing, the antibodies were added and incubated. Fluorescence was measured by using SpectroMax Microplate reader (Bio-Tek Instruments) at 450 nm. All samples were analyzed in duplicate.

Rat Experiment Setting.

Figure 9:
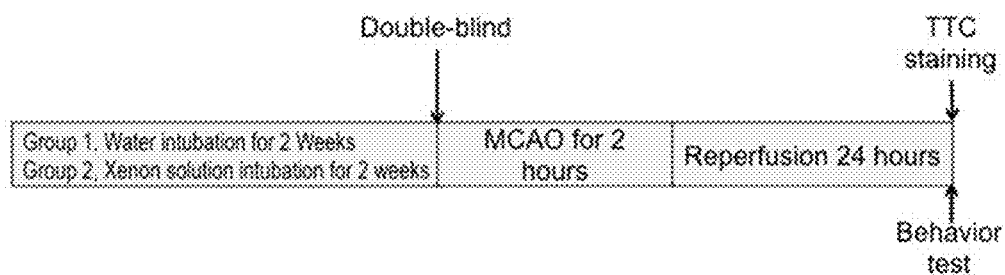
FIG. 9. Example of the rat experimental protocol.

Male Sprague-Dawley rats (260-280 g, Harlan Laboratories Inc., Indianapolis, Ind.) were randomly divided into two groups (n=8 in each group). One group was given water via a gastric tube and the other given the xenon-rich solution. After two weeks, the rats underwent middle cerebral occlusion for 2 hours in a double blind manner. Behavioral function was evaluated and then after scarifice, infarct volumes were evaluated at 24 hours after brain injury under a double blind manner. See FIG. 9.

Rat Model of Middle Cerebral Artery Occlusion (MCAO).

Cerebral ischemia was induced by occluding the right middle cerebral artery (MCA) for 2 hours using the intraluminal suture method. In brief, the right common carotid artery (CCA) was exposed under an operating microscope. The external carotid artery was ligated close to its distal end. The internal carotid artery (ICA) was isolated and separated from adjacent tissues. A 4-0 monofilament nylon suture (Ethicon, Somerville, N.J., USA) coated with poly L-lysine (0.1% [wt/vol]) and heparin (1000 U/mL) was inserted into the MCA lumen located 18 to 20 mm from the external carotid artery/common carotid artery bifurcation for 2 hours to provoke ischemia. As soon as the suture was removed, external carotid artery was ligated, allowing blood reperfusion through common carotid artery into MCA. In all experiments, body temperature was monitored and maintained at 37° C. during ischemia and over the first hour of reperfusion with the use of a feed-forward temperature controller equipped with a heating lamp and heating pad (Harvard Apparatus, Holliston, Mass., USA). A polyethylene catheter was introduced into the right femoral artery for pressure recording. Cerebral blood flow was monitored with the use of a PR407-1 straight-needle laser Doppler flowmeter probe (Perimed, Järfälla, Stockholm, Sweden) connected to a standard laser Doppler monitor (PF5010 LDPM unit and PF5001 main unit; Perimed, Järfälla, Stockholm, Sweden). Interruption of blood flow was recorded in the region of ischemic penumbra (2 mm lateral and 2 mm posterior to the bregma).

Neurologic Assessment.

Neurologic assessment was conducted at 24 hours after brain injury. All behavioral tests were conducted in a quiet and low-lit room by an observer blinded with respect to the treatment groups. Animals were tested for motor function and neurologic outcomes by recording limb placement, beam walking, and grid walking abilities.

Infarct Volume Measurement.

After neurologic assessment at 24 hours after surgery, animals were sacrificed and the brains harvested. Using a Jacobowitz brain slicer, 2-mm thick coronal sections were stained with 2% TTC. Infarct size was normalized with respect to the whole brain volume and presented as normalized infarct volume (%).

Statistical Analysis.

Data were processed using Microsoft Excel and GraphPad Prism 5.0. All values are expressed as the mean±S.E.M. Comparisons between each of two groups was determined using the unpaired 2-tailed Student's t test. Analysis of multiple groups was performed using one-way ANOVA, followed by a Tukey's post hoc multiple comparison test. P values of less than 0.05 were considered significant.

Example 2—Xe Administration Studies

Resistance to Cardiac Hypertrophy in Response to Xenon (Xe) Exposure.

To examine the effect of Xe activity on heart disease an apolipoprotein E knockout (apoE−/−; or "KO" as used herein) mouse model was employed. This is a well-established model for atherosclerosis, as the animals will develop atherosclerotic lesions even on a normal chow diet, while a high fat diet significantly accelerates this process (Meir et al., 2004). Accordingly, the model has previously been successfully employed to evaluate the effects of both natural compounds and pharmaceuticals on atherosclerosis and cardiovascular disease.

Animals were divided into 5 groups (see experiment setting). Echocardiography was used to assess cardiac dimensions and function at baseline, and at 6-weeks following the Xe exposure (FIGS. 1 and 2; Table 1). Cardiac size of WT and KO hearts were determined with LV mass (corrected) and normalized to body weight (mg/g) following 6-weeks of the Xe exposure (FIG. 3A).

As expected, LV mass increased in Apo E KO mice fed with/without high fat diet at 6-weeks and baseline versus WT and WT after 6 weeks, respectively. The increase in LV mass was blocked in KO mice treated with Xe (KO6w Xe) as compared to the KO6w vehicle and KO6w control groups. The presence of a hypertrophic heart was confirmed in that heart weight normalized to body weight was significantly increased in the KO6w control and vehicle groups. Decreased heart-to-body weight was observed in the KO6w Xe mice in response to the Xe exposure at 6 weeks, compared to the KO6w vehicle (FIG. 3B).

Figure 1A:
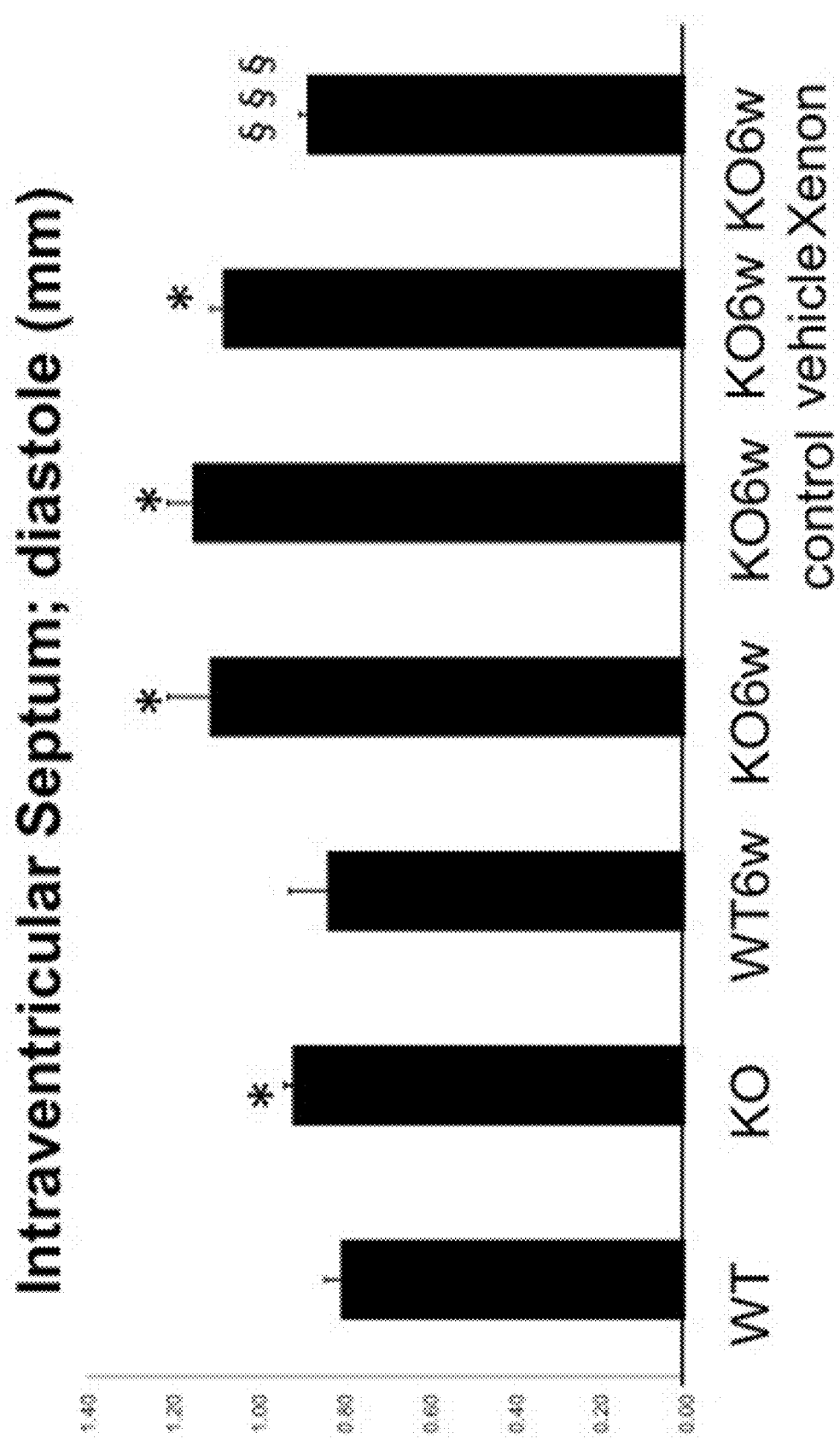
FIGS. 1A-1C. Echocardiographic Measurements to Assess Cardiac Hypotrophy and Function of C57BL/6J wild type (WT) and apolipoprotein-E (ApoE) knockout (KO) mice in Response to Xe-rich Solution Pre-treatment.
Figure 1B:
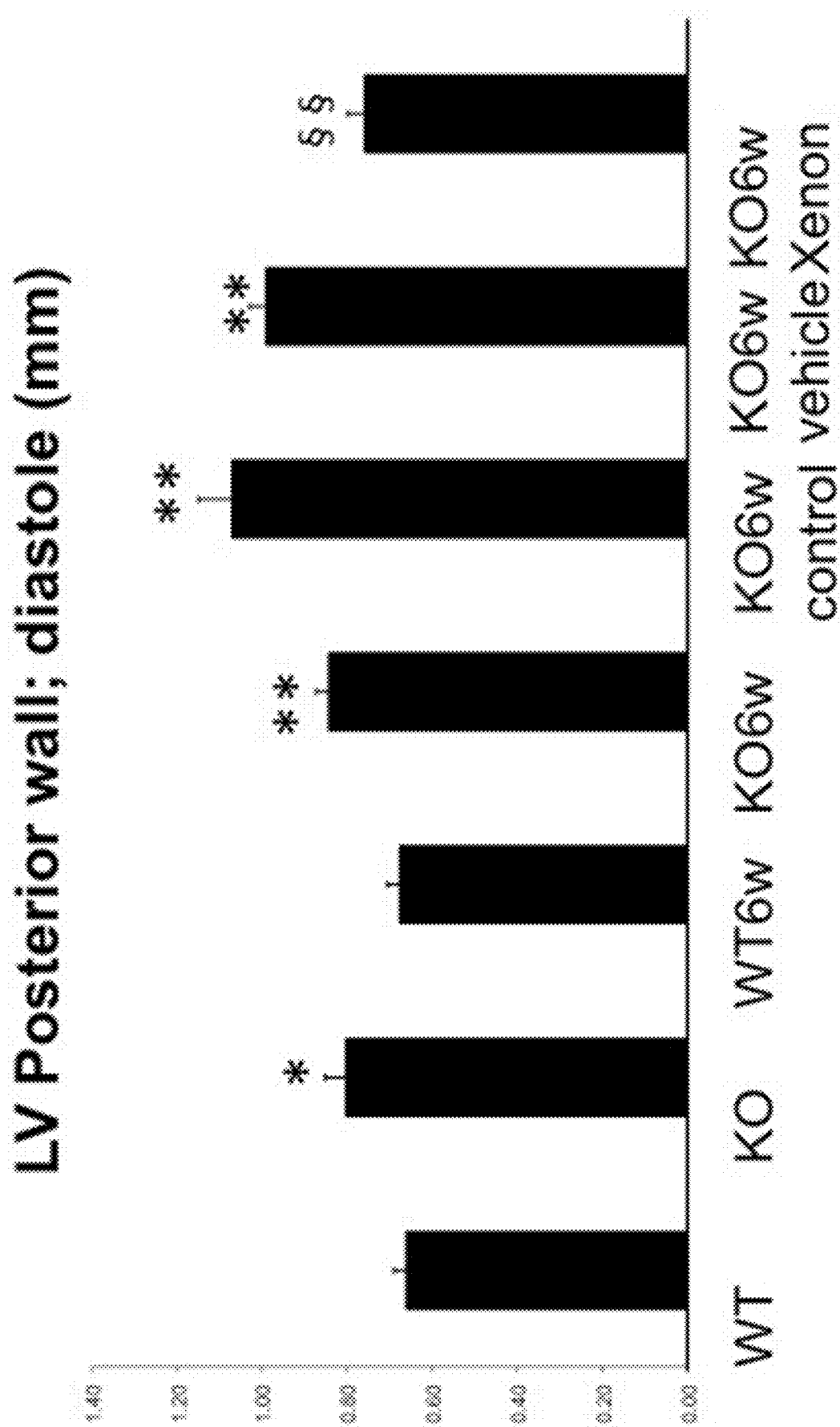
Figure 1C:
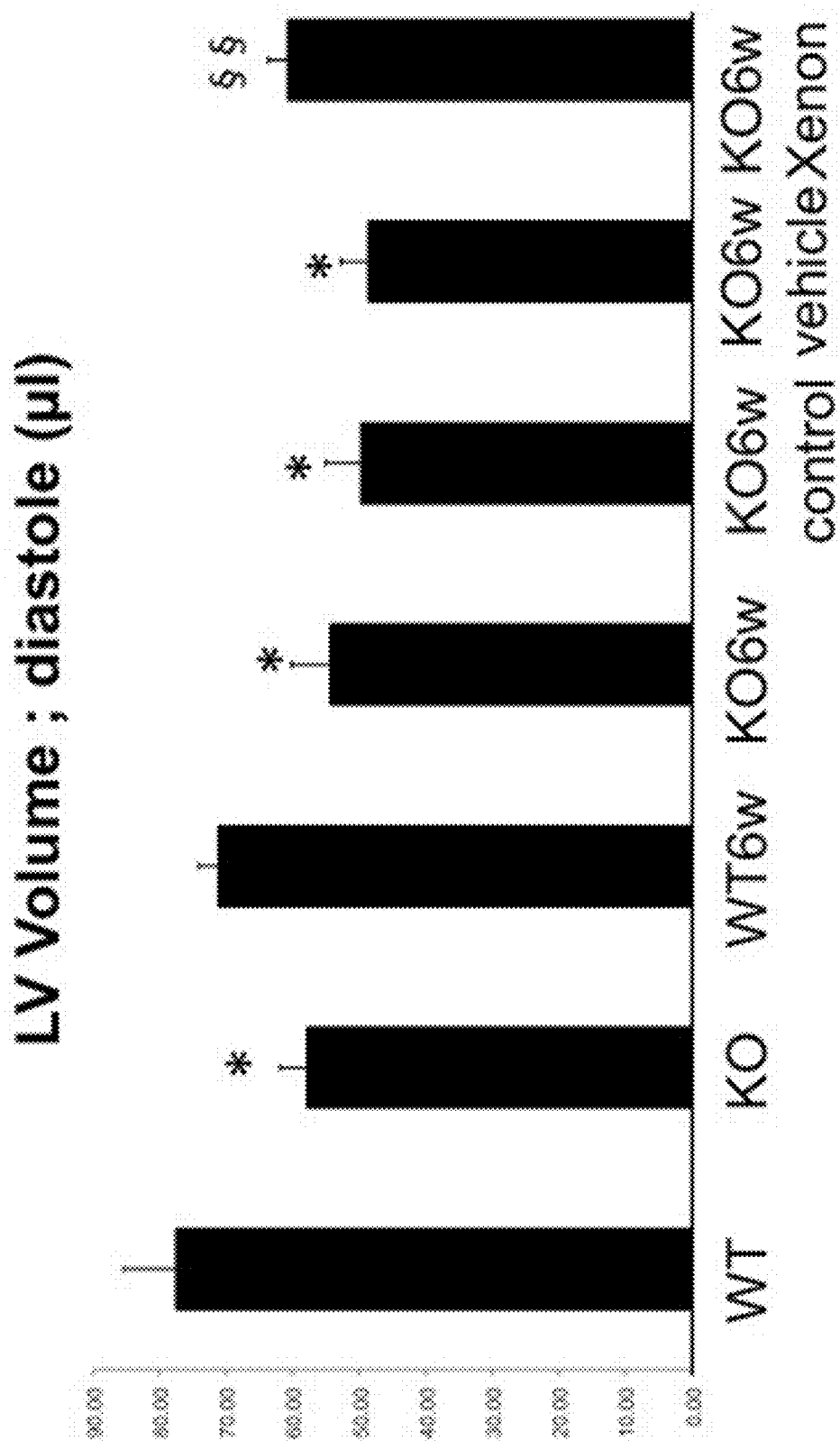
Figures 4A, 4B:
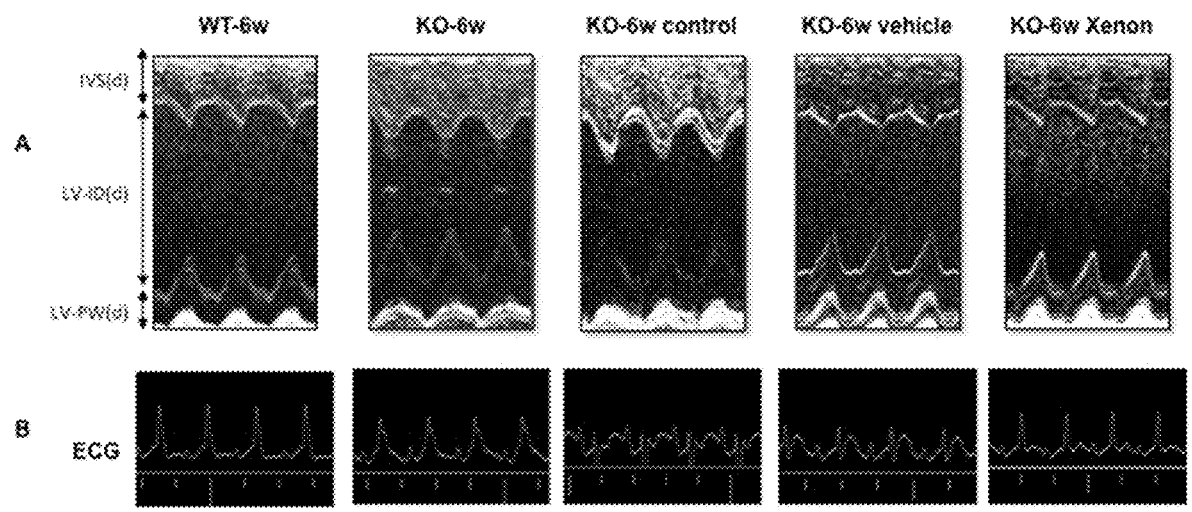
FIGS. 4A-4B. Myocardiographic Alterations in Cardiac Function in Wild Type and Apo-E Knockout Mice in response to Xe-rich Solution Pre-treatment. WT (n=9): wild type mice fed with regular diet at baseline; KO (n=25): Apo E-KO mice fed with regular diet at baseline. WT-6w (n=5): WT mice fed with regular diet for $6^{th}$ week. KO-6w (n=5): the KO mice fed with regular diet for $6^{th}$ week. KO-6w control (n=4): the KO mice fed with high fat diet and administered by PBS gavage for $6^{th}$ week. KO-6w vehicle (n=7): the KO fed with high fat diet and vehicles for $6^{th}$ week. KO-6w Xenon (n=6): the KO fed with high fat diet and administered with Xenon-rich-solution for $6^{th}$ week.

Intra-ventricular septum (IVS), LV posterior wall thickness (PW), LV volume (V), and LV internal dimensions (ID) were measured by echocardiography at baseline and following 6 weeks of Xe exposure a diastole and systole, in WT and ApoE-KO hearts (FIGS. 1A-1C and Table 1). The in wall thickness increase was significantly blocked in KO6w Xe mice in response to Xe exposure at 6 weeks, as compared to the KO6w vehicle mice, as well as versus KO6w/control mice (FIGS. 1A and 1B). Heart rate (HR) increased in KO/KO6w/control/vehicle animals compared to WT and WT6w, respectively. Again, this increase was blocked in KO6w given Xe (representative M-mode data are shown in FIG. 4A). Taken together, these results indicate that Xe activity suppresses progression of cardiac hypertrophy.

Improved Cardiac Function and Myocardial Ischemia in Response to Xe Exposure.

Figures 2A, 2B, 2C:
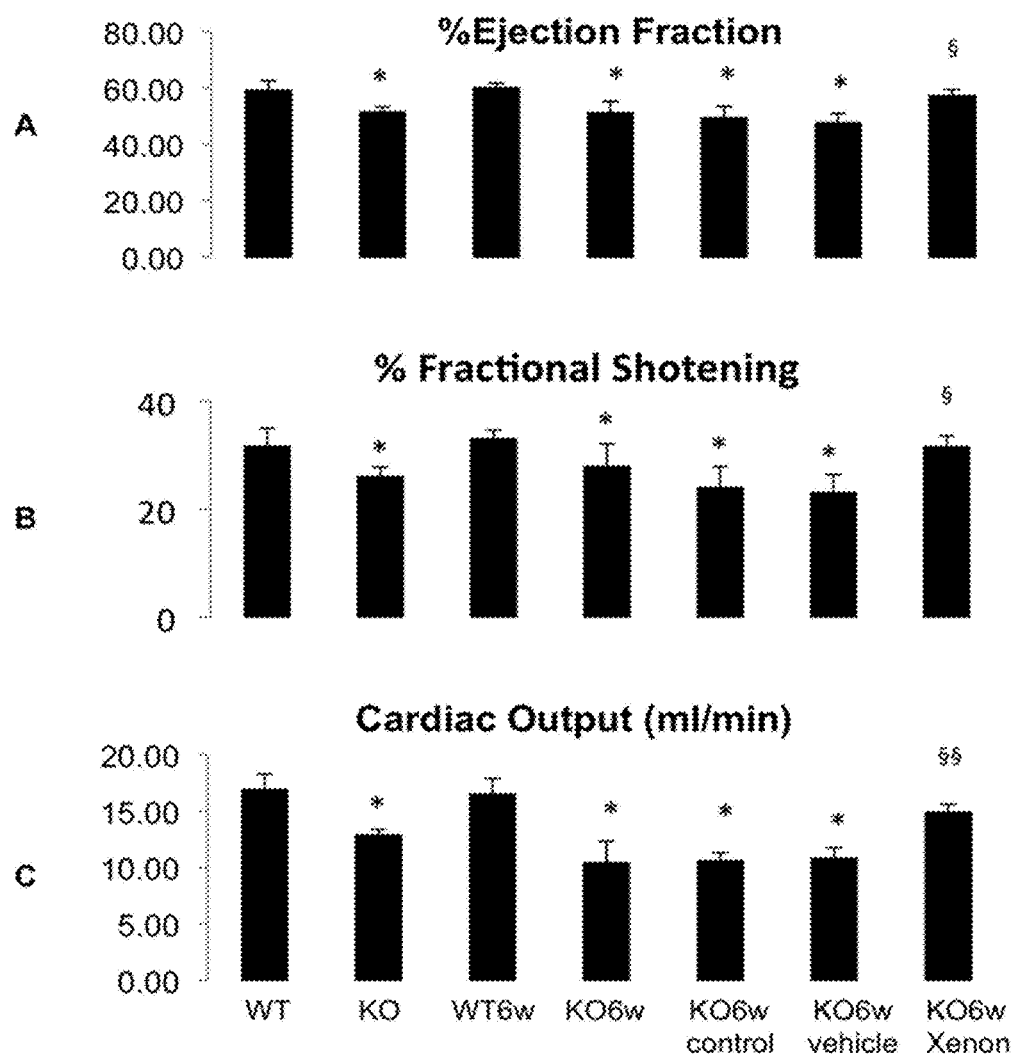
FIGS. 2A-2C. Echocardiographic Measurements on % Ejection fraction (% EF) (FIG. 2A). % Fractional shortening (% FS) (FIG. 2B), and Cardiac output (ml/min)(FIG. 2C). $*p<0.05$, $**\ p<0.01$, KO/KO6w compared to WT/WT6w, respectively; $\#p<0.05$, KO control/vehicle compared to KO6w; $\S\ p<0.05$, $\S\S\ p<0.01$, $\S\S\S\ p<0.001$, KO xenon compared to KO vehicle.
Figures 3A, 3B:
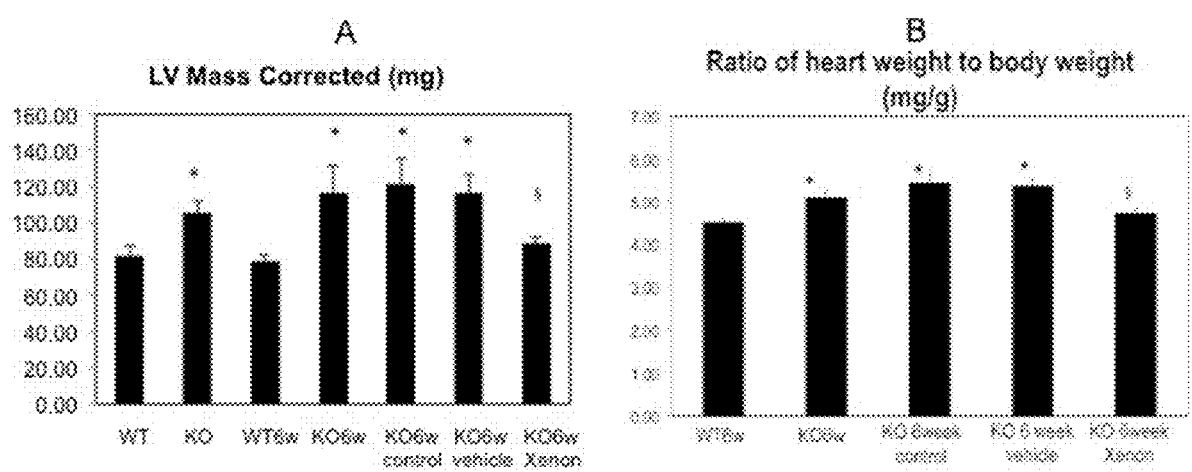
FIGS. 3A-3B. Alterations in Cardiac Mass Morphology in Wild Type (WT) and Apo-E Knockout (KO) Mice.

Cardiac function was assessed at baseline and 6 weeks following Xe exposure (FIGS. 2A-2C). At baseline and 6 weeks, LV fractional shortening (FS), LV ejection fraction (EF), and cardiac output (CO) were decreased in KO mice fed with/without high fat diet, as compared to WT and WT6w, respectively. On the other hand, KO6w Xe hearts, in response to Xe exposure, significantly blocked these decreases at 6 week time point as compared to KO6w vehicle (FIGS. 2A-2C; respectively).

ECG data show changes in T wave, ST segment, and QRS complex in KO/KO6w/control/vehicle hearts compared to WT/WT6w, respectively, consistent with myocardial ischemia. However, these changes did not occur in KO6w treated with Xe at the 6-weeks time point. These data indicate an improvement in myocardial ischemia in response to Xe exposure and suggest that Xe-treated hearts have no hypertrophic changes and less myocardial ischemia. These changes also suggest a protective role of xenon-rich solution in heart diseases (FIG. 4B and suggest that Xe activity improves cardiac function and protects from myocardial ischemia.

Increased Expression of BDNF in Heart and Brain Pretreated with Xe.

Figure 5A:
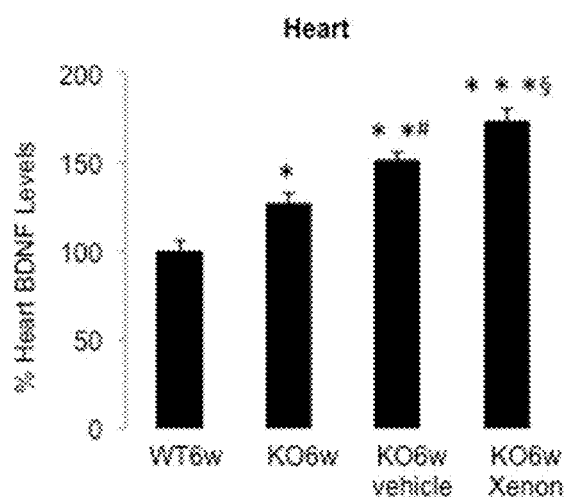
FIGS. 5A-5B. Levels of Brain-derived Neurotrophic Factor (BDNF) in the Heart (FIG. 5A) and Brain (FIG. 5B) in Response to Xe-Rich-Solution Per-treatment. WT-6w (n=4): WT mice fed with regular diet for $6^{th}$ week. KO-6w (n=5): the KO mice fed with regular diet for $6^{th}$ week. KO-6w vehicle (n=7): the KO fed with high fat diet and administered by the solution gavage at $6^{th}$ week. KO-6w Xenon (n=6): the KO fed with high fat diet and administered by Xenon gavage at $6^{th}$ week. $*p<0.05$, $\ p<0.01$, $*\ p<0.001$, KO6w/vehicle/Xenon compared to WT6w, respectively; $\#p<0.05$, KO6w vehicle compared to KO6w; $\S\ p<0.05$, KO6w Xenon compared to the vehicle.
Figure 5B:
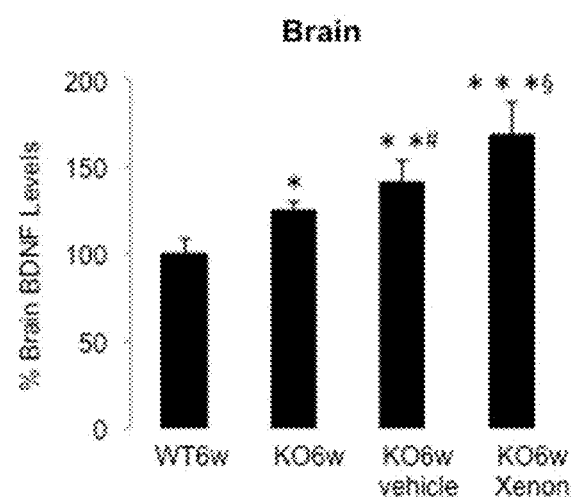

Xe preconditioning has the roles of neuroprotection in stroke (Peng et al, CNS Neurosci Ther; 2013 October; 19(10):773-84) and in brain damage from neonatal asphyxia (Ma et al, Journal of Cerebral Blood Flow & Metabolism (2006),199-208) in rats via the regulation of genes and synthesis of BDNF. Previous studies have shown that BDNF is expressed in heart and may be involved in the molecular mechanisms of heart disease (Okada et al., 2012). To assess the possible role of BDNF in Xe activity on the cardiovascular system, relative BDNF expression levels in heart and brain were measured by ELISA in the presence of absence of XE treatment (FIGS. 5A-5B). As shown in FIG. 5A, relative BDNF levels were increased in KO6w/control/vehicle, as compared to WT6w. Further increased BDNF levels were observed in KO6w vehicle versus KO6w. In response to Xe exposure BDNF levels were further increased in the heart (KO6w Xe). Similar results were also observed in brain (FIG. 5B). These data indicate that in the heart and brain, BDNF may be involved in Xe-mediated changes (Pagel et al., 2010).

Levels of β-Amyloid in Plasma and Brain Pretreated with Xenon-Rich Solution.

Figures 6A, 6B:
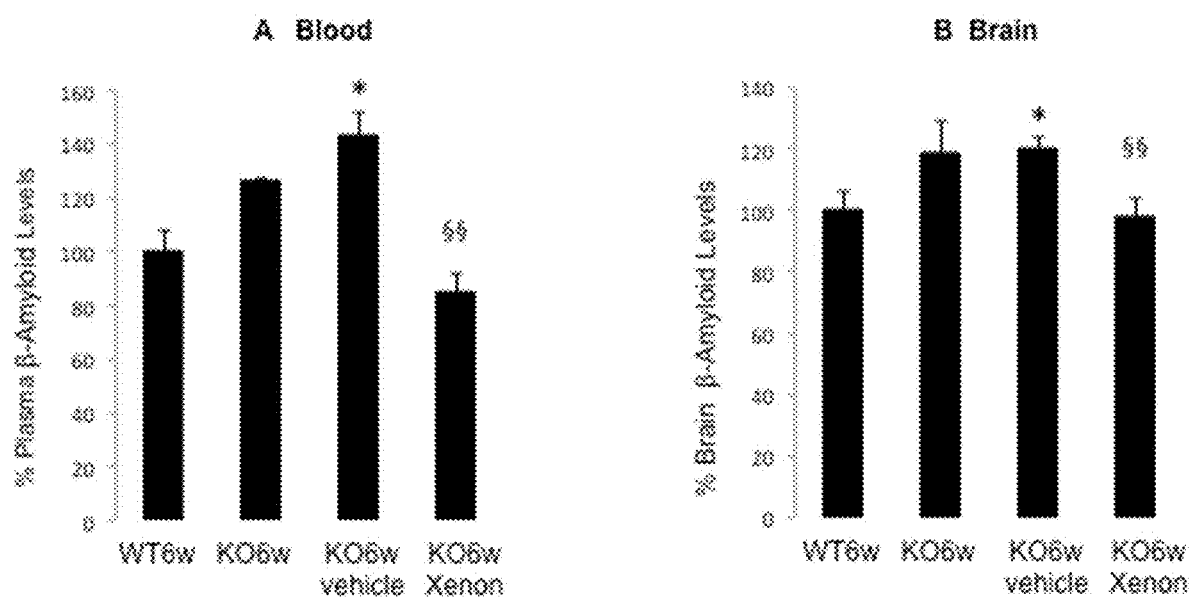
FIGS. 6A-6B. Levels of Beta-Amyloid in the Blood (FIG. 6A) and Brain (FIG. 6B) in Response to Xe-Rich-Solution Per-treatment. WT-6w (n=5): WT mice fed with regular diet for $6^{th}$ week. KO-6w (n=4): the KO mice fed with regular diet for $6^{th}$ week. KO-6w control (n=5): the KO mice fed with high fat diet and administered by PBS gavage for $6^{th}$ week. KO-6w vehicle (n=7): the KO fed with high fat diet and vehicles for $6^{th}$ week. KO-6w Xenon (n=6): the KO fed with high fat diet and administered by Xenon-rich-solution for $6^{th}$ week. $*p<0.05$, KO6w vehicle compared to WT6w; $\S\S\ p<0.01$, KO6w Xenon compared to the vehicle.

It has previously been reported that Xe may be involved in lipid homeostasis, however the exact role and effects of Xe on such homeostasis was unclear (Golden et al., 2010; Jung et al., 2011). β-amyloid is a main component of brain deposits associated with Alzheimer's disease and also is related to lipid homeostasis (Shankar et al., 2008; Selkoe et al., 2001). To investigate whether Xe activity could regulate β-amyloid levels Apo E-KO mice fed with high fat diets were examined. In particular, β-amyloid levels in the plasma and brains of treated and untreated animals were examined by ELISA (FIGS. 6A-6B). As shown in FIG. 6A, relative plasma β-amyloid levels were significantly increased in KO6w animals treated with the vehicle (and increase, although not significantly in KO6w) as compared to WT6w animals. This increase was markedly attenuated in KO6w mice given Xe-rich solution. Similar results were also observed in brain tissue (FIG. 6B). Importantly, these data demonstrate that administration of a Xenon-rich solution has the potential for treatment of cerebral deposition disease. Accordingly, such solution may be used to attenuate the effects or delay the progression of amyloid disease, such as Alzheimer's disease.

Xenon-Rich Solution to Increase Brain Tolerance to Ischemic Injury.

Figure 7A:
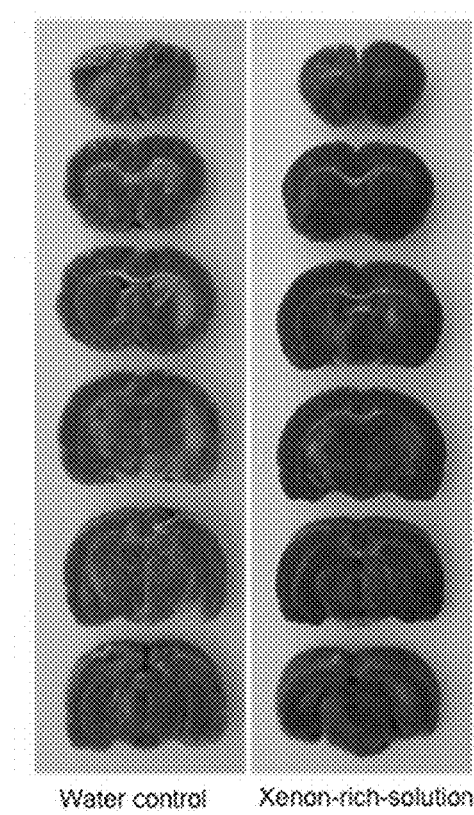
FIGS. 7A-7D. Xenon-rich-Solution to Increase Brain Tolerance to Ischemic Injury.
Figure 7B:
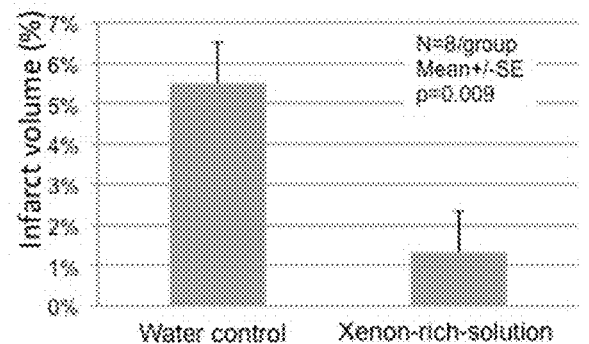
Figure 7C:
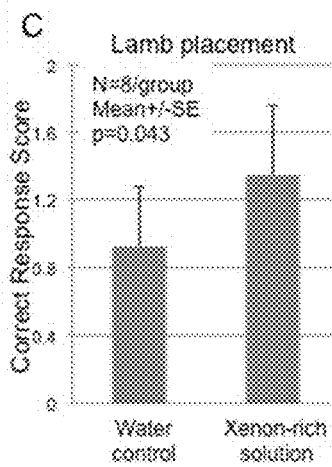
Figure 7D:
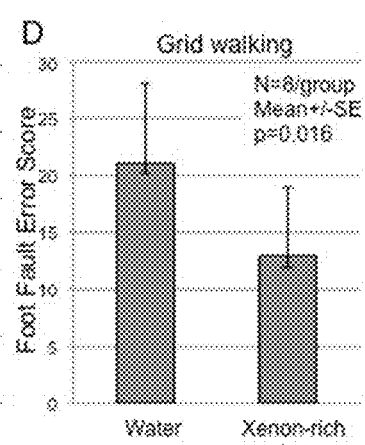

For these studies rats were divided into two groups, one group was given gastric delivery with water and another group was given gastric delivery with xenon-rich-solution. After two weeks, the rats underwent middle cerebral occlusion for 2 hours. Infarct volumes were evaluated at 24 hours after the brain injury. Rats given the xenon-rich solution developed smaller infarct size than controls (FIGS. 7A and 7B). Likewise, behavioral assessments including limb placement (FIG. 7C) and grid walking (FIG. 7D), which are indicative of neurological function were completed. The group pre-treated with an oral Xe-rich solution showed better ability to perform the behavioral tasks. These data indicate that administration of a xenon-rich-solution increases the brain tolerance to ischemic insults and can result in significant abatement of neurological effects even following significant ischemic injury.

Summary.

Studies presented here demonstrate the beneficial effects of oral Xe delivery for the neurological and cardiovascular systems. In particular, it has been shown that Xe intake was protective in a model system of cardiovascular disease, where an wide range of disease markers could be improved by Xe treatment. Likewise, it has been shown that oral Xe is neuroprotective. Not only was the orally delivered Xe able to significantly protect from ischemic injury, but Xe was also shown to reduce beta-amyloid load in treated animals, indicating that it may be useful in treatment or prevention of degenerative neurological disease. Importantly, the data also show that even in an oral delivery system (e.g., such a lipid system described herein) can deliver a sufficient amount of Xe to provide measurable benefit treated animals.

TABLE 1

| | Echocardiographic Measurements | | | | | |
|---|---|---|---|---|---|---|
| | LVID; d (mm) | IVS; s (mm) | LVID; s (mm) | LVPW; s (mm) | LV Vol; s (μL) | Heart Rate (BPM) |
| WT wild type mice fed with regular diet at baseline | 4.14 ± 0.18 | 1.26 ± 0.09 | 2.86 ± 0.12 | 1.11 ± 0.08 | 30.55 ± 5.34 | 360 ± 11 |
| KO Apo E-KO mice fed with regular diet at baseline | 3.6 ± 0.11* | 1.28 ± 0.07 | 2.65 ± 0.11 | 1.13 ± 0.04 | 27.99 ± 3.46 | 439 ± 9* |
| WT6 w WT mice fed with regular diet for 6 weeks | 4.01 ± 0.05 | 1.18 ± 0.07 | 2.66 ± 0.08 | 1.18 ± 0.07 | 29.67 ± 3.38 | 377 ± 15 |
| KO6 w KO mice fed with regular diet for 6 weeks | 3.4 ± 0.22* | 1.32 ± 0.10 | 2.42 ± 0.13 | 1.2 ± 0.07 | 26.85 ± 2.83 | 428 ± 19* |
| KO6 w control KO mice fed with high fat diet and administered by PBS gavage for 6 weeks | 3.4 ± 0.16* | 1.34 ± 0.11 | 2.47 ± 0.09 | 1.41 ± 0.05 | 25.45 ± 4.19 | 459 ± 15* |
| KO6 w vehicle KO fed with high fat diet and vehicles for 6th week | 3.4 ± 0.14* | 1.36 ± 0.06 | 2.57 ± 0.10 | 1.3 ± 0.05 | 26.26 ± 3.71 | 457 ± 14 |

TABLE 1-continued

| | Echocardiographic Measurements | | | | | |
|---|---|---|---|---|---|---|
| | LVID; d (mm) | IVS; s (mm) | LVID; s (mm) | LVPW; s (mm) | LV Vol; s (μL) | Heart Rate (BPM) |
| KO6 w Xenon KO fed with high fat diet and administered with Xenon-rich-solution for 6th week | 4.0 ± 0.07[§§] | 1.29 ± 0.05 | 2.65 ± 0.10 | 1.26 ± 0.07 | 26.01 ± 3.82 | 402 ± 13[§] |

*p < 0.05,
**p < 0.01, KO/KO6 w compared to WT/WT6 w, respectively;
# p < 0.05, KO control/vehicle compared to KO 6 w;
[§]p < 0.05,
[§§]p < 0.01,
[§§§]p < 0.001, KO xenon compared to KO vehicle.
Vehicle is caged molecular water with cyclodextrin without Xenon loaded.

Example 3—Material and Methods for Example 4

Preparation of Caged Molecular Enclosed Xenon

Xenon was enclosed into a soluble caged molecules (e.g., cyclodextrin). To remove possible residue molecules from cage, the caged molecular was baked at 40-80° C. under vacuum for overnight. To enclose xenon into caged molecules, xenon was incubated with caged molecular in a sealed vial under 2-10 atm pressure at 4 to −180° C. for overnight to 3 days.

Preparation of Pure Xenon Supersaturated Water

Pure water was degassed under 20-80 mbar vacuum at room temperature for overnight. Xenon (99.999% Medical grade, Matheson Tri-Gas®, Houston, Tex., USA) was re-dissolved into degassed water by pressure water with 2-10 atm xenon gas at 4° C. for overnight to 3 days.

Preparation of Xe-Rich-Water

Xe-rich-water is composed of Xe directly dissolved in water and caging with hydroxypropyl-beta-cyclodextrin (hp-beta-CD) in water. To prepare a Xe-rich-water, Xenon supersaturated water (10 ml) was injected into the vial containing 5 mg caged molecular-xenon complexes (0.5 mg/ml). The resulting mixture was incubated under 2-10 atm pressure at 4° C. for overnight to 3 days.

Measurement of Xe Dissolved in Xenon-Rich-Water

To measure the amount of Xe dissolved in a Xe-rich-water. The solution was warmed to room temperature and the pressure over Xe-rich-water sample was released. The solution was then warmed up to 80° C. in a vial with a silicone-rubber seal (Thermo Scientific SepraSeal®) (Thermo Scientific, Hudson, N.H., USA) sealed top for 2 hours. After cooling down to room temperature, a syringe with a 17 gauge needle was inserted into a vial through the silicone-rubber seal. The released Xe gas present in the top spacer formed pressure, which pushed Xe gas into the syringe. The amount of Xe released into syringe was then measured.

Animals

All animal studies were approved by the Animal Welfare Committee at The University of Texas Health Science Center at Houston. Wild type (WT) and Apo E knockout (KO) transgenic mice were purchased from Jackson Laboratory (Bar Harbor, Me., USA). Wild type control mice used were C57BL/6J to compare with the Apo E KO mice with the same genetic background. Eight- to eleven-month old male and female WT and KO mice were fed with a high fat diet (Harlan Laboratories, USA) and administered with caged molecular water with CD, but without Xe (vehicle) or Xe-rich-water, which included caged molecular water with CD loaded with Xe (0.2 to 10 ml per day) for 6 weeks.

Echocardiographic Measurements and Electrocardiographic Images (In Vivo)

Baseline measurements by echocardiography were obtained before feeding with the high fat diet. Cardiac morphology and function were assessed by serial M-mode echocardiography using a Vevo 770 Imaging System (VisualSonics Inc., Ontario, Canada) equipped with a 30 MHz microprobe. M-mode ventricular measurements were taken at 6-weeks after the feeding. Electrocardiographic (ECG) data was obtained. Echo data (HR, heart rate; LVID, left ventricular internal dimension; IVS, intra-ventricular septum; LVPW, left ventricular posterior wall; FS, fractional shortening; SV, stroke volume; EF, ejection fraction; CO, cardiac output; LV Vol, LV volume; LV mass corrected) were analyzed with the analysis software (VisualSonics Inc., Ontario, Canada).

Blood Pressure Measurement

Mice blood pressure was monitored non-invasively utilizing a tail-cuff placed on mice tail to occlude the blood flow.

Protein Assays

Fresh frozen heart and brain tissues were slightly thawed on crushed ice to allow dissection of the hearts and brains. Tissue samples were homogenized by sonicating for 2-3 bursts of 20 seconds on ice using a minimal volume of radioimmunoprecipitation assay (RIPA) buffer (Cell Signaling Technology, Inc. MA. USA)) containing protease inhibitors (complete protease inhibitor cocktail, Sigma) and centrifuged for 10 min at 4° C. at 14,000×g. The supernatant was removed. The protein concentration was determined by using a Bradford Protein Assay (Bio-Rad, Calif., USA)

β-Amyloid Measurements

β-amyloid peptide (Aβ1-40) content in both brain and blood were determined using a Mouse/Rat Amyloid β (1-40) High Specific ELISA Assay Kit (IBLAmerican, Minneapolis, Minn., USA). Following instructions, the samples were added in the pre-coated 96-well microtiter plates for incubation overnight at 4° C. After washing, the antibodies were added and incubated. Absorbance was measured by using SpectroMax Microplate reader (Bio-Tek Instruments) at 450 nm. All samples were analyzed in duplicate.

Western Blot Analysis Cardiac Troponin Expression in Heart Tissue

Western blot analysis was carried out as previously described (Yin, X, Molecular Pharmacology) using cardiac troponin I (cTnI) (Cell Signaling Technology, Inc., Danvers, Mass., USA). For immunoblot analyses, samples were resolved by SDS-PAGE (4-12%) gradient gels, and transferred to Polyvinilidene Fluoride (PVDF) membranes. Blots were then incubated overnight at 4° C. with primary antibodies and washed three times with TBS containing 0.1% Tween 20 (TBST), and then probed with secondary antibodies (LI-COR Biosciences, Lincoln, Nebr., USA) following the manufacturer's instructions. Densitometric analyses of the immunoblots were performed with an Odyssey Infrared Imager (LI-COR Biosciences).

Statistical Analysis

Data were processed using Microsoft Excel and GraphPad Prism 5.0. All values are expressed as the mean±S.E.M. Comparisons between two groups were determined using unpaired 2-tailed Student's t test. Analysis was performed using one-way ANOVA, followed by a Tukey's post hoc multiple comparison test when multiple groups were compared. P values of less than 0.05 were considered significant.

Example 4—Results of Further Studies with Xe Enhanced Water

Xenon Dissolved in Xe-Rich-Water

Cyclodextrin (CD) is a multifunctional caged molecule employed the in food, pharmaceutical, and chemical industries. Cyclodextrins provide a hydrophobic interior and a hydrophilic exterior. Studies described here were undertaken to determine if these properties could be used, to increase the solubility of Noble gases, such as xenon.

Figures 10A, 10B, 10C, 10D:
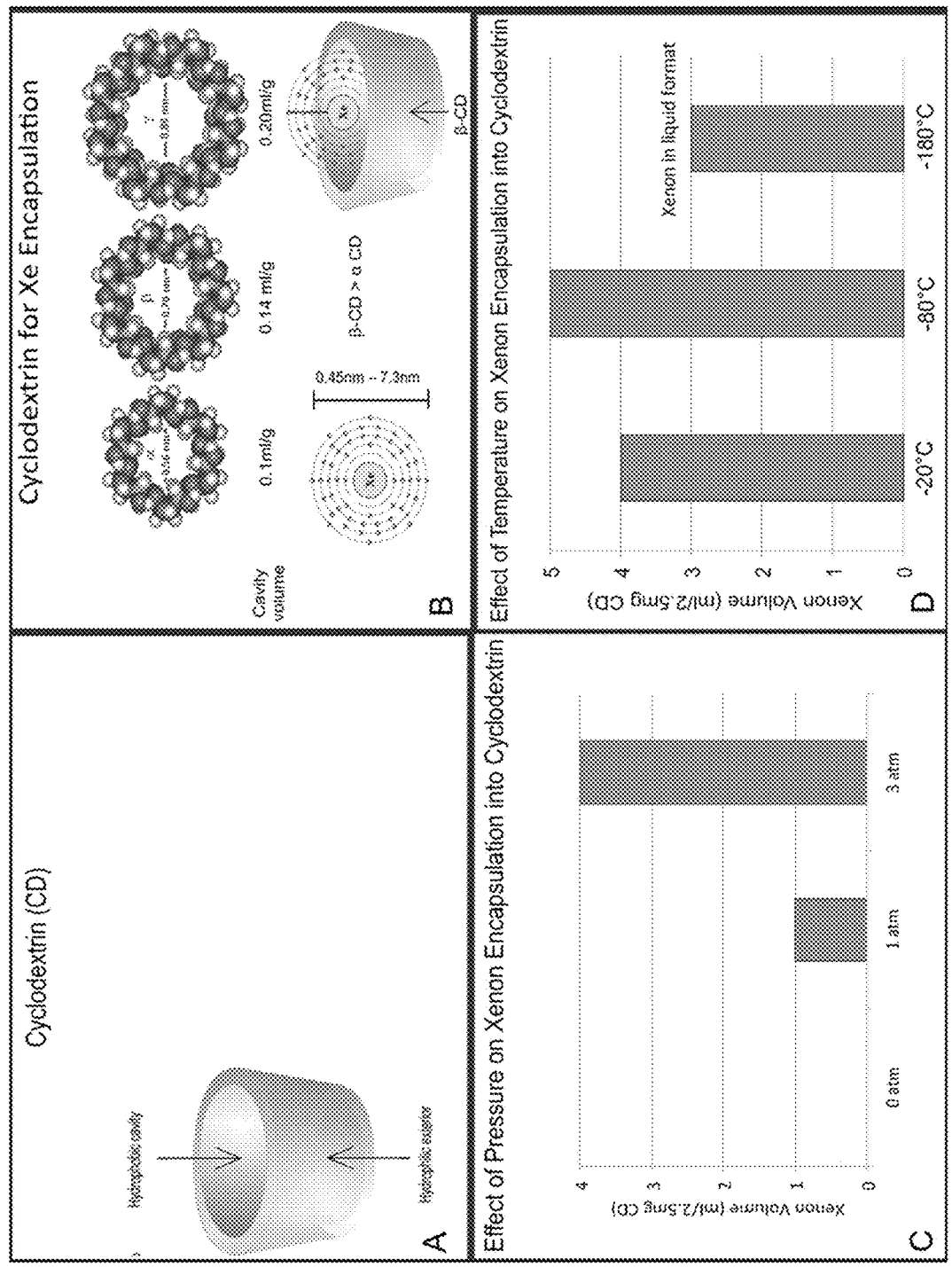
FIGS. 10A-10D. Initial Xenon caging experiments. (A) A schematic showing the structure of CD used for caging of Xe. (B) A schematic showing the physical properties of α-, β- and γ-CD as compared to a Xe atom. (C) Graph shows the results of studies to determine the effects of pressure on Xe encapsulation in CD. (D) Graph shows the effects of temperature on the on Xe encapsulation in CD.

Data from initial studies demonstrated that the inclusion of Xenon into cyclodextrin (hp-beta-CD) is highly related to pressure (FIG. 10C) and temperature (FIG. 10D). Increased pressure resulted in increased amounts of Xe encapsulation as shown in FIG. 10C. Likewise, encapsulation of gaseous Xe at low temperature was more efficient (FIG. 10D). For example, the studies showed that, at 3 atm, −80° C., a total of 5 ml of xenon could be encapsulated in a hp-beta-CD cage (0.5 mg/ml of hp-beta-CD was used).

Figure 11:
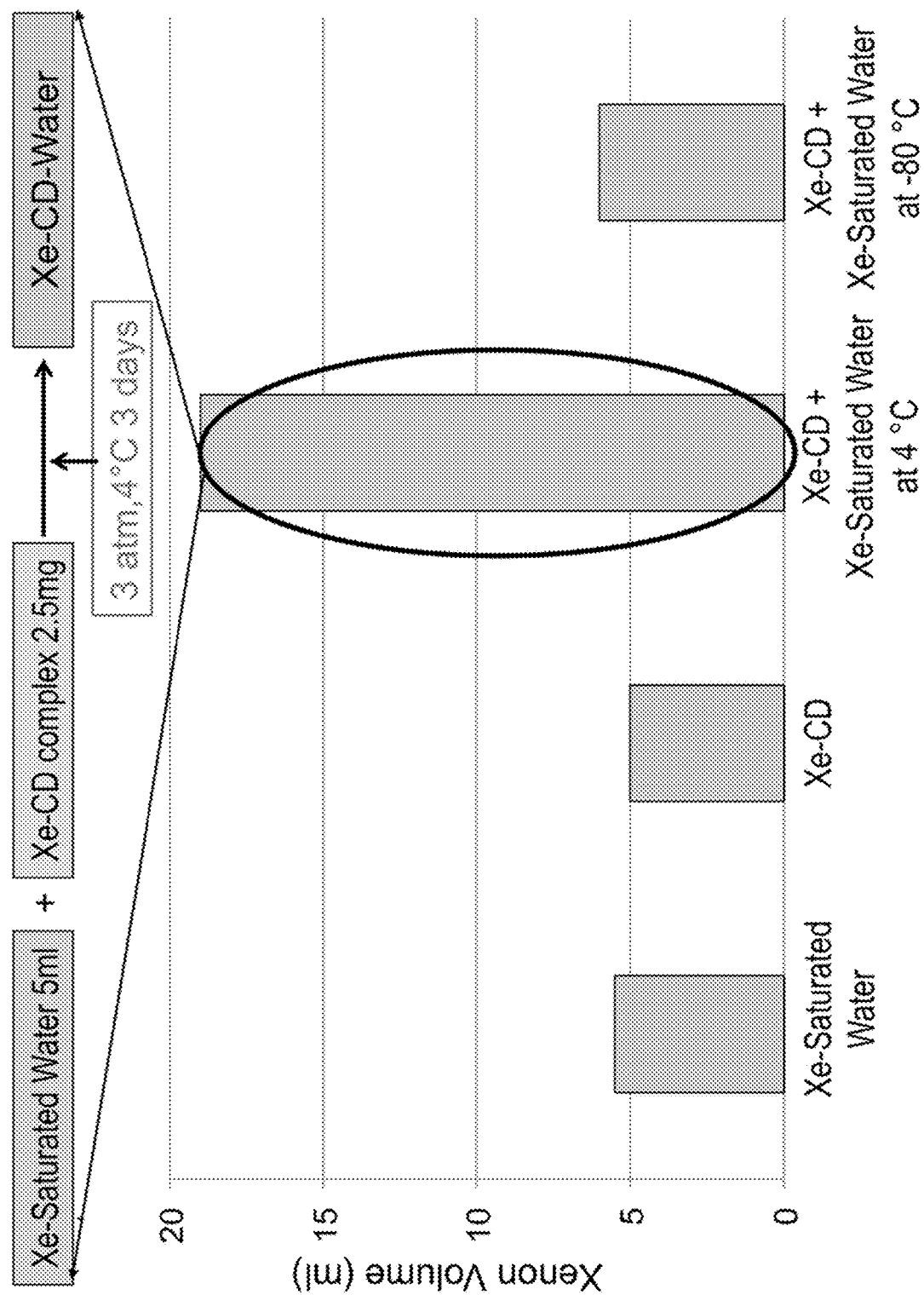
FIG. 11. Upper panel shows an exemplary protocol for production of Xe enhanced water using CD caging. Lower panel is a graph showing the volume of dissolved Xe per 5 ml water that was achieved using the indicated methods.

Xenon solubility in water is, likewise, highly related to the pressure and temperature of the solution. By incubation of degassed water with pure xenon gas at 4° C., 3 atm for 4 hours to overnight, a total 6.5 ml xenon gas was dissolved into 5 ml water. To make Xe-rich-water, Xe-saturated water was incubated with Xe-CD under 3 atm pressure at 4° C. A pressure of 3 atm was used here since, typically, a standard beverage container can withstand 80-90 psi (5.4-6.1 atm) pressure (i.e., a typical can of a soft drink such as Coca-Cola™ classic products have an internal pressure of 55 psi (3.7 atm) at 75° F.). As showed in FIG. 11, in the presence of water as a media, 19 ml Xenon gas was included into caged molecules and dissolved in water (with a starting volume of 5 ml of water). Thus, the formulation achieved a total Xe content of 22.4 mg Xe per ml of the CD-water solution (at CD concentration of 0.5 mg/ml hp-beta-CD).

Xenon-Rich-Water Increases the Tolerance of Heart to Ischemic Stress

To examine the effect of Xe activity on prevention of heart disease mice were divided into 4 groups, (1) wild type fed with normal food and water control (WT); (2) Apo E knockout mice fed with high fat diet and normal water control; (3) Apo E knockout mice fed with high fat diet and vehicle control (feed with water containing cyclodextrin but no xenon), and (4) Apo E knockout mice fed with high fat diet and Xe-rich-water (Xenon loaded into cyclodextrin, i.e. molecular caged xenon). Echocardiography was used to assess cardiac dimensions and function at baseline, and at 6-weeks after feeding.

Figures 12A, 12B, 12C:
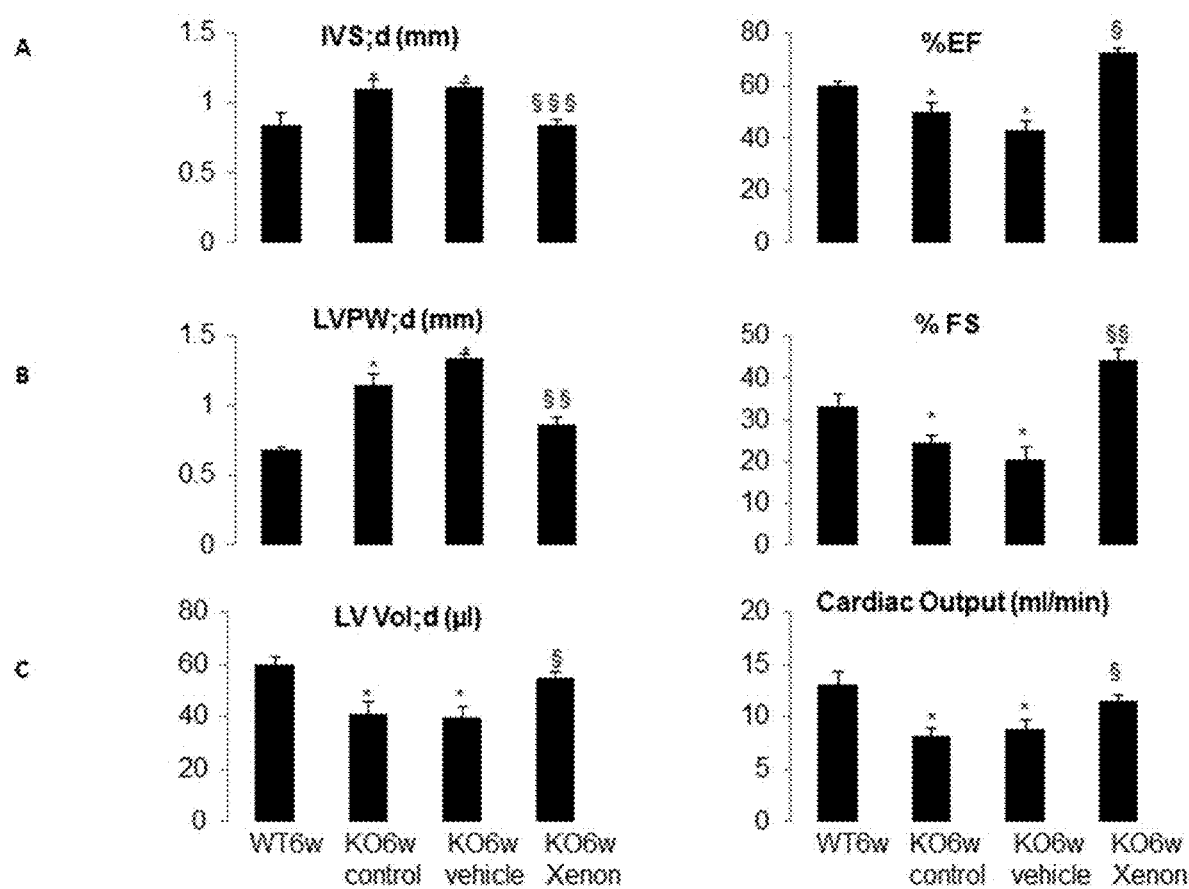
FIGS. 12A-12C. Echocardiographic Measurements of Mice Treated with Xe Water. Graphs show the results of echocardiographic measurement of (1) WT mice fed with regular diet for 6th week (WT-6w, n=5); (2) Apo E knockout mice fed with high fat diet and normal water control (KO6w control, n=13); (3) vehicle control mice feed with water containing cyclodextrin only (KO6w vehicle, n=5); or (4) Apo E knockout mice fed with Xe-rich-water (KO6w Xenon, n=5) after 6 weeks of treatment. Graphs show the results of measurements of intra-ventricular septum (IVS) volume, percent left ventricular (LV) ejection fraction (EF), left ventricular posterior wall thickness (LVPW), percent LV fractional shortening (FS), LV volume and cardiac output (CO).

Intra-ventricular septum (IVS), left ventricular posterior wall thickness (LVPW), left ventricular (LV) volume, and LV internal dimensions (ID) were measured at diastole and systole by echocardiography at baseline and following 6-weeks of treatment (FIGS. 12A-12C). High fat diet caused the ventricular wall thickness to be significantly increased, as is typical for ApoE KO animals. However, this pathological change did not occur in ApoE KO mice receiving 6-weeks of Xe-rich-water treatment, as compared to mice which received only water with cyclodextrin (FIGS. 12A-12C). Heart rate (HR) also increased in ApoE KO mice fed a high fat diet and treated with vehicle. Again, treatment with Xe-rich-water prevented this increase. These results suggest, as indicated in the studies above, that oral Xe-rich-water consumption suppresses progression of cardiac hypertrophy. Furthermore, levels of Xe in the encapsulated water formulations were high enough to achieve beneficial effect.

Cardiac function was also assessed at baseline and 6-weeks of administration of Xe-rich-water (FIGS. 12A-12C). At baseline and 6-weeks, LV fractional shortening (FS), (EF), and cardiac output (CO) were decreased in ApoE KO mice fed with a high fat diet, as compared to WT and WT6w treated mice. In ApoE KO mice that received administration of Xe-rich-water (KO6w Xe) hearts from the mice significantly protected from these decreases as compared to KO6w vehicle at the 6-week time point, (FIGS. 12A-12C; respectively).

ECG data show changes in T wave, ST segment, and QRS complex in KO/KO6w/control/vehicle hearts compared to WT/WT6w respectively, compatible with myocardial ischemia. These changes did not occur in the hearts of ApoE KO mice that received administration of Xe-rich-water (KO6wXe hearts) 6-weeks. This indicates that administration of Xe-rich-water reduces myocardial ischemia.

Troponin and CKMB (Creatine Kinase) are two markers of heart ischemia. Further studies measured the plasma CKMB level and troponin expression in heart tissue. These studies showed that the level of the two markers were increased in controls and was decreased in ApoE KO mice that received administration of Xe-rich-water (FIGS. 13A-13B). These data further confirmed that the consumption of Xe-rich water increased the tolerance of the heart to ischemic stress.

Xenon-Rich-Water Stabilize Blood Pressure

Further analysis of Xe-treated mice indicated that oral administration of the Xe-rich drinking water on a daily basis for 6 weeks significantly decreases both systolic and diastolic blood pressure (Table 2), while increasing the heart contractility.

TABLE 2

Xe-rich-water stabilize blood pressure

|  | Baseline (n = 19) | ApoE 6W-control (n = 3) | ApoE 6W-vehicle (n = 5) | ApoE 6W-Xenon (n = 5) |
|---|---|---|---|---|
| Systolic BP (mmHg) | 98 ± 7 | 122 ± 4* | 121 ± 5* | 103 ± 3§ |
| Diastolic BP (mmHg) | 74 ± 5 | 94 ± 3* | 91 ± 2* | 77 ± 3§ |

*$p < 0.05$, KO/KO6W compared to Apo E fed without high fat diet (baseline);
§$p < 0.05$, KO Xenon compared to KO vehicle Xenon-Rich-Water Reduces Beta-Amyloid in Both Brain Tissue and Blood Studies were also undertaken to determine the effects of Xe-water administration on β-amyloid in brain and blood (see FIGS. 14A-14B). For these studies the well characterized ApoE-KO mouse model system for Alzheimer's disease was used. These mice exhibit increased levels of serum and brain β-amyloid levels as compared to control mice. However, administration of Xe-water to the mice over a period of six weeks resulted in decreased levels of both serum and brain β-amyloid (achieving levels similar to control animals).

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,981,687
U.S. Pat. No. 5,089,477
U.S. Pat. No. 5,147,650
U.S. Pat. No. 5,236,712
U.S. Pat. No. 5,238,684
U.S. Pat. No. 7,976,743
U.S. Pat. Publn. No. 20030177784
Adams et al., *J. Phys. Chem. A,* 112(30):6829-6839, 2008.
Baumert et al., *Acta Anaesthesiol. Scan.,* 49:743-749, 2005.
Cao et al., *Angewandte Chemie International Edition.* 48(51):9721-9723, 2009.
Golden et al., *PLoS One,* 5:e10099, 2010.
Hein et al., *Acta Anaesthesiol. Scan.,* 54:470-478, 2010.
Huang, Sl, circulation
Jung et al., *Eur. J. Appl. Physiol.,* 111:303-311, 2011.
Meir et al., "Atherosclerosis in the Apolipoprotein E-Deficient Mouse—A Decade of Progress," *Arterioscler. Thromb. Vasc. Biol.,* 24:1006-1014, 2004.
Okada et al., *Arteriosclerosis, Thrombosis, and Vascular Biol.,* 32:1902-1909, 2012.
Pagel, *J. Cardiothorac. Vasc. Anesth.,* 24:143-163, 2010.
Saleh "Novel Phenomena In Encapsulating Hydrocarbon Gases," in Novel Phenomena In Encapsulating Hydrocarbon Gases, 2007.
Selkoe, *Neuron,* 32:177-180, 2001.
Skelton et al., *Phys Chem Chem Phys.* 15(12):4341-54, 2013.
Shankar et al, *Nat. Med.,* 14:837-842, 2008.

What is claimed is:

1. A method for treating cardiovascular disease or injury in a subject, comprising orally administering a composition comprising an aqueous component comprising dissolved Xe gas, a portion of the Xe gas being encapsulated with a water-soluble polymer, wherein the water-soluble polymer comprises alpha-cyclodextrin, beta-cyclodextrin, and/or gamma-cyclodextrin.

2. The method of claim 1, wherein the cardiovascular disease is atherosclerosis, thrombotic stroke, hemorrhage stroke, heart failure or cardiac hypertrophy.

3. The method of claim 1, wherein the composition comprises 500 mg to 10 g, 500 mg to 5 g, 500 mg to 2 g, 1 to 100 mg, 1 to 50 mg, 1 to 25 mg or 1 to 10 mg of Xe.

4. The method of claim 1, wherein the water-soluble polymer comprises gamma-cyclodextrin.

5. The method of claim 1, wherein the water-soluble polymer comprises alpha- and gamma-cyclodextrin.

6. The method of claim 1, wherein the composition comprises 0.05 to 2.0 mg/ml of the alpha-cyclodextrin, beta-cyclodextrin, and/or gamma-cyclodextrin.

7. The method of claim 1, wherein the composition further comprises phospholipid, detergent, or protein components.

8. The method of claim 1, wherein the composition is further defined as an herbal, vitamin, or energy-providing nutraceutical beverage.

9. The method of claim 1, wherein the subject has atherosclerosis, thrombotic stroke, hemorrhage stroke, ischemic stroke, heart failure, or cardiac hypertrophy.

10. The method of claim 1, wherein the subject has atherosclerosis.

11. The method of claim 1, wherein the subject has high blood pressure.

12. The method of claim 1, wherein the composition provides reduced blood pressure in the subject.

* * * * *